US008287923B2

(12) United States Patent
Hsu et al.

(10) Patent No.: US 8,287,923 B2
(45) Date of Patent: Oct. 16, 2012

(54) COMPOSITIONS AND METHODS FOR TREATING IMMUNE DISORDERS

(75) Inventors: Stephen D. Hsu, Evans, GA (US); Carol A. Lapp, Augusta, GA (US); George S. Schuster, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 1050 days.

(21) Appl. No.: 11/916,832

(22) PCT Filed: Jun. 9, 2006

(86) PCT No.: PCT/US2006/022554
§ 371 (c)(1),
(2), (4) Date: May 28, 2008

(87) PCT Pub. No.: WO2006/135785
PCT Pub. Date: Dec. 21, 2006

(65) Prior Publication Data
US 2009/0062379 A1 Mar. 5, 2009

Related U.S. Application Data

(60) Provisional application No. 60/689,747, filed on Jun. 10, 2005.

(51) Int. Cl.
*A61K 36/82* (2006.01)
*A61K 31/352* (2006.01)
*A61P 37/02* (2006.01)
(52) U.S. Cl. .................. 424/729; 514/456; 514/885
(58) Field of Classification Search .................. None
See application file for complete search history.

(56) References Cited

U.S. PATENT DOCUMENTS

| | | |
|---|---|---|
| 4,235,871 A | 11/1980 | Papahadjopoulos |
| 4,501,728 A | 2/1985 | Geho |
| 4,624,665 A | 11/1986 | Nuwayser |
| 4,655,767 A | 4/1987 | Woodard |
| 4,687,481 A | 8/1987 | Nuwayser |
| 4,797,284 A | 1/1989 | Loper |
| 4,810,499 A | 3/1989 | Nuwayser |
| 4,834,978 A | 5/1989 | Nuwayser |
| 4,837,028 A | 6/1989 | Allen |
| 4,877,618 A | 10/1989 | Reed |
| 4,880,633 A | 11/1989 | Loper |
| 4,917,895 A | 4/1990 | Lee |
| 4,920,016 A | 4/1990 | Allen |
| 4,927,687 A | 5/1990 | Nuwayser |
| 4,956,171 A | 9/1990 | Chang |
| 5,019,369 A | 5/1991 | Presant |
| 5,035,894 A | 7/1991 | Lee |
| 5,091,186 A | 2/1992 | Miranda |
| 5,163,899 A | 11/1992 | Sibalis |
| 5,232,702 A | 8/1993 | Pfister |
| 5,234,690 A | 8/1993 | Chiang |
| 5,273,755 A | 12/1993 | Venktrama |
| 5,273,756 A | 12/1993 | Fallon |
| 5,308,625 A | 5/1994 | Wong |
| 5,356,632 A | 10/1994 | Gross |
| 5,358,715 A | 10/1994 | Wong |
| 5,372,579 A | 12/1994 | Sibalis |
| 5,421,816 A | 6/1995 | Lipkovker |
| 5,466,465 A | 11/1995 | Royds |
| 5,494,680 A | 2/1996 | Peterson |
| 5,505,958 A | 4/1996 | Bello |
| 5,554,381 A | 9/1996 | Roos |
| 5,560,922 A | 10/1996 | Chien |
| 5,585,111 A | 12/1996 | Peterson |
| 5,656,285 A | 8/1997 | Sablotsky |
| 5,667,798 A | 9/1997 | Royds |
| 5,698,217 A | 12/1997 | Wilking |
| 5,741,511 A | 4/1998 | Lee |
| 5,747,783 A | 5/1998 | Myung |
| 5,770,219 A | 6/1998 | Chiang |
| 5,814,599 A | 9/1998 | Mitragotri |
| 5,817,332 A | 10/1998 | Urtti |
| 5,833,647 A | 11/1998 | Edwards |
| 5,879,322 A | 3/1999 | Lattin |
| 5,906,830 A | 5/1999 | Farinas |
| 6,248,341 B1 * | 6/2001 | Anderson et al. |

FOREIGN PATENT DOCUMENTS

| | | |
|---|---|---|
| JP | 9176010 | 7/1997 |
| JP | 9227374 | 9/1997 |

OTHER PUBLICATIONS

Uchida K, et al. Immunology (Sep. 2005): 116(1): 53-63. Identification of specific autoantigens in Sjögren's syndrome by SEREX.*
Allen, et al. "Drug delivery systems: entering the mainstream." *Science*. 303(5665):1818-22 (2004).
Azuma et al. "Immortalization of normal human salivary gland cells with duct-, myoepithelial-, acinar-, or squamous phenotype by transfection with SV40 ori-mutant deoxyribonucleic acid," *Lab Invest*. 69(I):24-42(1993).
Balant et al. "Prodrugs for the improvement of drug absorption via different routes of administration", *Eur. J. Drug Metab. Pharmacokinet*, 15(2): 143-53(1990).
Balimane and Sinko "Involvement of multiple transporters in the oral absorption of nucleoside analogues", *Adv. Drug Delivery Rev.*, 39(1-3): 183-209(1999).
Baudouin, et al. "Current treatments of xerophthalmia in Sjögren's syndrome," *Rev Med Interne*. 25(5):376-82(2004).
Beck, et al. "A new long-acting injectable microcapsule system for the administration of progesterone" *Fertil. Steril*. 31 :545-51(1979).
Benita, et al. "Characterization of drug-loaded poly(d,l-lactide) microspheres," *J. Pharm. Sci*. 73: 1721(1984).
Billings, et al. "Xerostomia and associated factors in a community-dwelling adult population," *Community Dent Oral Epidemiol*. (5):3 12-6(1996).
Bolstad et al. "Increased salivary gland tissue expression of Fas, Fas ligand, cytotoxic T lymphocyte-associated antigen 4, and programmed cell death 1 in primary Sjögren's syndrome," *Arthritis Rheum* 48:174-85(2003).

(Continued)

*Primary Examiner* — Michele C. Flood
(74) *Attorney, Agent, or Firm* — Pabst Patent Group LLP

(57) ABSTRACT

Green tea polyphenol compositions and methods of their use are provided. Certain aspects provide methods for modulating expression of one or more autoantigens using the disclosed green tea polyphenol compositions. Representative green tea polyphenols include, but are not limited to (−)-epigallocatechin-3-gallate. Other aspects provide methods for treating autoimmune disease.

5 Claims, 9 Drawing Sheets

OTHER PUBLICATIONS

Borchardt, et al. "Improvement in peptide bioavailability: Peptidomimetics and Prodrug Strategies", *Adv. Drug. Delivery Rev.* 27:235-256(1997).

Browne "Fosphenytoin (Cerebyx)", *Clin. Neuropharmacol.* 20(1): 1-12(1997).

Callen, "Update on the management of cutaneous lupus erythematosus," *Br. J. Dematol.* 151(4):731-6) (2004).

Carsons, "A review and update of Sjögren's syndrome: manifestations, diagnosis, and treatment," *Am J Manag Care.* 7(14 Suppl):S433-43.24(2001).

Cassolato, et al. "Xerostomia: clinical aspects and treatment." *Gerodontology.* 20(2):64-77(2003).

Cha, et al. "Progress in understanding autoimmune exocrinopathy using the non-obese diabetic mouse: an update," *Crit. Rev. Oral Biol. Med.* 13:4-16(2002).

Daniels and Fox, "Salivary and oral components of Sjögren's syndrome," *Rheum. Dis. Clin. North Am.* 18(3):571-89(1992).

Daniels and Wu, "Xerostomia—clinical evaluation and treatment in general practice," *Calif Dent Assoc.* 28(12):933-41(2000).

Farquhar, et al. "Biologically Reversible Phosphate-Protective Groups," *J. Pharm. Sci.*, 72(3): 324-325(1983).

Fleisher et al. "Design of prodrugs for improved gastrointestinal absorption by intestinal enzyme targeting," *Methods Enzymol.* 112: 360-81(1985).

Fleisher et al. "Improved oral drug delivery: solubility limitations overcome by the use of prodrugs," *Adv. Drug Delivery Rev.* 19(2): 115-130(1996).

Fox, "Sjögren's syndrome. Controversies and progress," *Clin Lab Med.* 17(3):431-44(1997).

Fox, "Sjogren's syndrome: evolving therapies," *Expert Opin Investig Drugs.* 12(2):247-54(2003).

Han,et al. "Targeted prodrug design to optimize drug delivery," *AAPS PharmSci.*, 2(1): E6(2000).

Hsu, et al. "Inhibition of Autoantigen Expression by (−)-Epigallocatechin-3-gallate (the Major Constituent of Green Tea) in Normal Human Cells," *JPET* 315:805-811(2005).

Hsu, et al. "Green tea polyphenols reduce autoimmune symptoms in a murine model for human Sjogren's syndrome and protect human salivary acinar cells from TNF-alpha-induced cytotoxicity," *Autoimmunity* 40(2):138-47(2007).

Hsu, et al. A new approach to managing oral manifestations of Sjogren's syndrome and skin manifestations of lupus, *J Biochem Mol Biol*.39(3):229-39(2006).

Hsu, et al. Green tea polyphenol induces caspase 14 in epidermal keratinocytes via MAPK pathways and reduces psoriasiform lesions in the flaky skin mouse model. *Exp. Derm.* 16(8):678-84(2007).

Ikebe, et al. "Perception of dry mouth in a sample of community-dwelling older adults in Japan," *Spec Care Dentist.* 21(2):52-9(2001).

Khurshudian, "A pilot study to test the efficacy of oral administration of interferon-alpha lozenges to patients with Sjögren's syndrome," *Oral Surg Oral Med Oral Pathol Oral Radiol Endod.* 95(1):38-44(2003).

Lambert "Rationale and applications of lipids as prodrug carriers," *Eur. J. Pharm. Sci.*, 11 Suppl 2:S15-27(2000).

Mathiowitz, et al. "Morphology of polyanhydride microsphere delivery systems ,"*J. Scanning Microscopy* 4:329-40(1990).

Mathiowitz, et al., "Novel Microcapsules for Delivery Systems" *Reactive Polymers* 6: 275-283 (1987).

Miyasaka, "Epidemiology and pathogenesis of Sjögren's syndrome," *Nippon Rinsho* 53(10):2367-70 (1995).

Mizen et al. (1998). "The use of esters as prodrugs for oral delivery of beta-lactam antibiotics," *Pharm. Biotech.* I I,:345-365.

Porter, et al. "An update of the etiology and management of xerostomia," *Oral Surg Oral Med Oral Pathol Oral Radiol Endod.* 97(I):28-46(2004).

Rehman,"Sjögren's syndrome," *Yonsei Med J.* 44(6):947-54) (2003).

Sadzuka, Effective prodrug liposome and conversion to active metabolite, *Curr Drug Metab.*, I(I):31-48(2000).

Schein, et al. "Dry eye and dry mouth in the elderly: a population-based assessment" *Arch Intern Med.* 159(12): 1359-63(1999).

Stinton, et al. "Autoantibodies to protein transport and messenger RNA processing pathways: endosomes, lysosomes, Golgi complex, proteasomes, assemblysomes, exosomes, and GW bodies," *Clin Immunol.* 110(I):30-44(2004).

Szoka et al., "Comparative properties and methods of preparation of lipid vesicles (liposomes)," *Ann. Rev. Biophys. Bioeng.* 9: 467-508 (1980).

Vitali, et al, "Classification criteria for Sjögren's syndrome: a revised version of the European criteria proposed by the American-European Consensus Group," *Ann Rheum Dis.* 61(6):554-8(2002).

Wang et al. "Prodrug approaches to the improved delivery of peptide drug," *Curr. Pharm. Design.* 5(4):265-287(1999).

Wang, et al. "Prodrug approaches to the improved delivery of peptide drugs." *Curr. Pharm. Des.*, 5(4):265-87(1999).

Yoshida, "Sjögren's syndrome," *Nippon Rinsho* 57(2):360-3(1999).

Zhang,"Epidemiological study of primary Sjogrne's syndrome in China," *Chin Med J* (Engl). 108(10)787-8(1995).

Medical College of Georgia (Apr. 25, 2003). "Green Tea Linked to Skin Cell Rejuvenation." *ScienceDaily*. Retrieved Feb. 5, 2008, from http://www.sciencedaily.com /releases/2003/04/030425071800.htm.

\* cited by examiner

SEQUENCE LISTING

<160> NUMBER OF SEQ ID NOS: 6

<210> SEQ ID NO 1
<211> LENGTH: 18
<212> TYPE: DNA
<213> ORGANISM: artificial sequence
<220> FEATURE:
<223> OTHER INFORMATION: primer

<400> SEQUENCE: 1
tcccatcacc atcttcca                                                       18

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
catcacgcca cacgagtttc c                                                   21

<210> SEQ ID NO 3
<211> LENGTH: 22
<212> TYPE: DNA
<213> ORGANISM: artificial sequence
<220> FEATURE:
<223> OTHER INFORMATION: primer

<400> SEQUENCE: 3
gaactgctgc aggaggtgat aa                                                  22

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
ggcacattca gagaaggagt                                                     20

<210> SEQ ID NO 5
<211> LENGTH: 27
<212> TYPE: DNA
<213> ORGANISM: artificial sequence
<220> FEATURE:
<223> OTHER INFORMATION: primer

```
<400> SEQUENCE: 5
ccaaaatctg tcatcaaatt gagtatt                                          27

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
ccagccttca tccagtttta tct                                              23
```

COMPOSITIONS AND METHODS FOR TREATING IMMUNE DISORDERS

CROSS-REFERENCE TO RELATED APPLICATION

This application is a filing under 35 U.S.C. §371 of PCT/US2006/022554 filed with the U.S. Receiving Office of the Patent Cooperation Treaty on Jun. 9, 2006, which claims benefit of and priority to U.S. Provisional Patent Application No. 60/689,747, filed on Jun. 10, 2005, and where permissible is incorporated by reference in its entirety.

STATEMENT REGARDING FEDERAL FUNDING OR SUPPORT

This invention was made with Government Support under Grant No. R21 CA097258-01 A1 awarded by the National Institutes of Health. The Government has certain rights in the invention.

BACKGROUND

1. Technical Field

Aspects of the disclosure are generally related to compositions and methods for modulating autoantigen expression, more particularly to green tea polyphenol compositions and methods of their use, for example in the treatment or prophylaxis of autoimmune disorders.

2. Related Art

The prevalence of autoimmune disorders in the United States is estimate at more than 8.5 million. Autoimmune reactions can cause inflammation and apoptosis of target cells, leading to destruction of multiple tissues and organs. Patients with autoimmune diseases develop autoantibodies against a diverse group of macromolecules involved in normal functions. For example, anti-SS-A/Ro and anti-SS-B/La autoantibodies are primary markers for certain autoimmune diseases such as lupus erythematosus and Sjögren's syndrome. Existing treatments of autoimmune diseases have focused on the immune system, not the autoantigens that could trigger or sustain a positive feedback loop of inflammation and apoptosis.

Lupus Autoimmune Disorders

Lupus is one of more than 60 types of autoimmune disorders, and is one of the most destructive. Clinical classification of lupus includes systematic lupus erythematosus (SLE), discoid lupus ecrythematosus (DLE), subacute cutaneous lupus (SCLE), drug induced lupus, and neonatal lupus. SLE is the most prevalent form and may affect, multiple tissues such as joints, skin, kidneys, heart, lungs, blood vessels, and brain. It affects mostly young females of childbearing age. Lupus can cause severe joint and muscle pain, extreme exhaustion, fevers, and skin rashes, and can lead to organ failure, scars and death. The skin manifestations of S LE arid DLE are slightly different. DLE affects mainly the skin and the oral cavity with disk-shaped lesions while SLE affects multiple organs. Skin manifestations occur in about 25% of SLE patients, with butterfly shaped lesions distributed on the face and ears. It is believed that cutaneous LE affects 14.6 to 68 per 100 000 people (Callen, J. P. (2004) Br J. Dematol. 151(4):731-6).

Sjögren's Syndrome

Sjögren's syndrome (SS) is another autoimmune disorder that affects multiple tissues. Primary SS is associated with lymphocytic infiltrations of the salivary and lacrimal glands and eventual atrophy, leading to a loss of fluid production. The salivary component of SS is defined as xerostomia, with symptoms generally referred to as salivary hypofunction (Daniels, T. E. and Fox, R. I. (1992). Rheum Dis Clin North Am. 18(3):571-89). If not treated, xerostomia may lead to oral complications (Daniels T. E. and Wu, A J. (2000) Calif Dent Assoc. 28(12):933-41). Estimates of the prevalence of SS are affected by the criteria used for diagnosis. However, genuine differences between various regions and communities exist (Fox, R. I. (1997) Clin Lab Med. 17(3):43 1-44; Vitali, C. et al, (2002) Ann Rheum Dis. 61(6):554-8). The world-wide distribution is believed to be 1/2500 (Kang, H. (1993)). In the United States, SS affects approximately 1% of the population (Carsons, S. (2001) Am J Manag Care. 7(14 Suppl):S433-43.24). In China, one regional study with 26,000 subjects suggested the prevalence of primary SS was only 0.03% (Zhang, N. (1995) Chin Med J (Engl). 108(10): 787-8). In Japan, the estimated crude prevalence rates for SS were only 1.9 and 25.6 per 100,000 population in males and females, respectively (Yoshida, S. (1999) Nippon Rinsho. 57(2):360-3). A survey conducted by the Japanese Ministry of Health and Welfare indicated the SS prevalence was just 0.06% among females (Miyasaka, N. (1995) Nippon Rinsho. 53(10):2367-70).

As for xerostomia, one study showed that among a group of 1003 Japanese individuals with an average age of 66, about 9.1% experienced dry mouth during eating (Ikebe, K. et al. (2001) Spec Care Dentist. 21(2):52-9), whereas in the United States, one epidemiological study found that in a group of 2481 individuals aged 65-84 years old, 27% reported either dry mouth or dry eyes (Schein, O. D. et al. (1999) Arch Intern Med. 159(12): 1359-63), and another found that dry mouth ranged from 10% among persons over age 50 to 40% for persons over age 65 (Billings R J., et al. (1996) Community Dent Oral Epidemiol. (5):3 12-6). Although precise statistical comparison between the U.S. population and either the Japanese or Chinese population is not available, it is apparent that SS and xerostomia are more prevalent in the U.S. population, particularly amongst the elderly.

SS is not a curable or preventable disease at present, and whether it can be prevented or delayed is unknown. Treatment is generally symptomatic and supportive. For xerostomia and xerophthalmia, artificial lubricants are commonly used as saliva or tear substitutes (Baudouin, C. et al. (2004) Rev Med Interne. 25(5):376-82). In recent years, salivary stimulants, such as pilocarpine and cevimeline, have been approved by the FDA to treat xerostomia (Fox, R. I. (2003) Expert Opin Investing Drugs. 12(2):247-54); Cassolato, S. F. and Turnbull, R. S. (2003) Cerodontology. 20(2):64-77; Porter, S. R. et al. (2004) Oral Surg Oral Med Oral Pathol Oral Radiol Endod. 97(1):28-46). In addition, oral administration of interferon γ (IFN-γ) was effective in improving saliva production in patients with primary SS (Khurshudian, A. V. (2003) Oral Surg Oral Med Oral Pathol Oral Radiol Endod. 95(1):38-44). However, long-term adverse effects have not been evaluated for these therapies.

Thus, there is a need for additional compositions and methods for preventing and treating autoimmune diseases or symptoms associated with such diseases.

SUMMARY

Aspects of the disclosure generally provide green tea polyphenol compositions and methods of their use, for example in decreasing autoantigen expression in a host or cell. In particular, it has been discovered that (−)-epigallocatechin-3-gallate modulates expression of autoantigens. Downregulation of autoantigens using the disclosed green tea polyphenol compositions can be used to treat autoimmune diseases or symptoms associated with autoimmune diseases. Increasing expression of autoantigens can be used to assist in the purification and isolation of autoantigens, for example to generate antibodies that can be used as diagnostics.

One aspect of the disclosure provides a method for decreasing autoantigen expression in a cell by contacting the cell with a composition having one or more green tea polyphenols. The cell contacted with the one or more green tea polyphenols shows a decreased level of autoantigen expression relative to a control. In certain aspects, the green tea polyphenol is (−)-epigallocatechin-3-gallate, a pharmaceutically acceptable salt or prodrug thereof. Representative autoantigens include those listed in Table 1, for example SS-A, SS-B, fodrin, centromere protein, golgin-67, coilin, and PARP. In other aspects, the composition further includes one or more green tea polyphenols such as (−)-epicatechin, (−)-epigallocatechin, (−)-epicatechin-3-gallate, proanthocyanidins, enantiomers thereof epimers thereof isomers thereof, combinations thereof, and prodrugs thereof. It will be appreciated that the disclosed methods and compositions can be used to modulate, in particular reduce the expression of at least two autoantigens relative to a control.

Another aspect provides a method for modulating autoantigen gene expression by administering to a host one or more green tea polyphenols in an amount effective to reduce or increase expression of an autoantigen gene compared to a control. Reduced expression of the autoantigen gene can occur at the transcriptional or translational level.

Still another aspect provides a method for treating an autoimmune disease by administering to a host one or more green tea polyphenols in an amount effective to decrease expression of one or more autoantigens. Representative autoimmune diseases include, but are not limited to Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, scieroderma, psoriasis, xerostomia, and xeropthalmia.

Another aspect provides a method for treating xerostomia by administering to a host one or more green tea polyphenols in an amount effective to decrease expression of one or more autoantigens, wherein the decreased expression of the one or more autoantigens occurs in one or more salivary gland cells of the host.

Yet another aspect provides a method for treating xerophthalmia by administering to a host one or more green tea polyphenols in an amount effective to decrease expression of one or more autoantigens in one or more of the host's lacrimal gland cells.

Still another aspect provides a method for treating psoriasis by administering to a host one or more green tea polyphenols in an amount effective to decrease expression of one or more autoantigens in one or more epidermal cells of the host.

Another aspect provides a use of a green tea polyphenol in the manufacture of a medicament for the treatment of an autoimmune disease, in particular, psoriasis, xerostomia, or xerophthalmia.

DETAILED DESCRIPTION

1. Definitions

Figure 1:
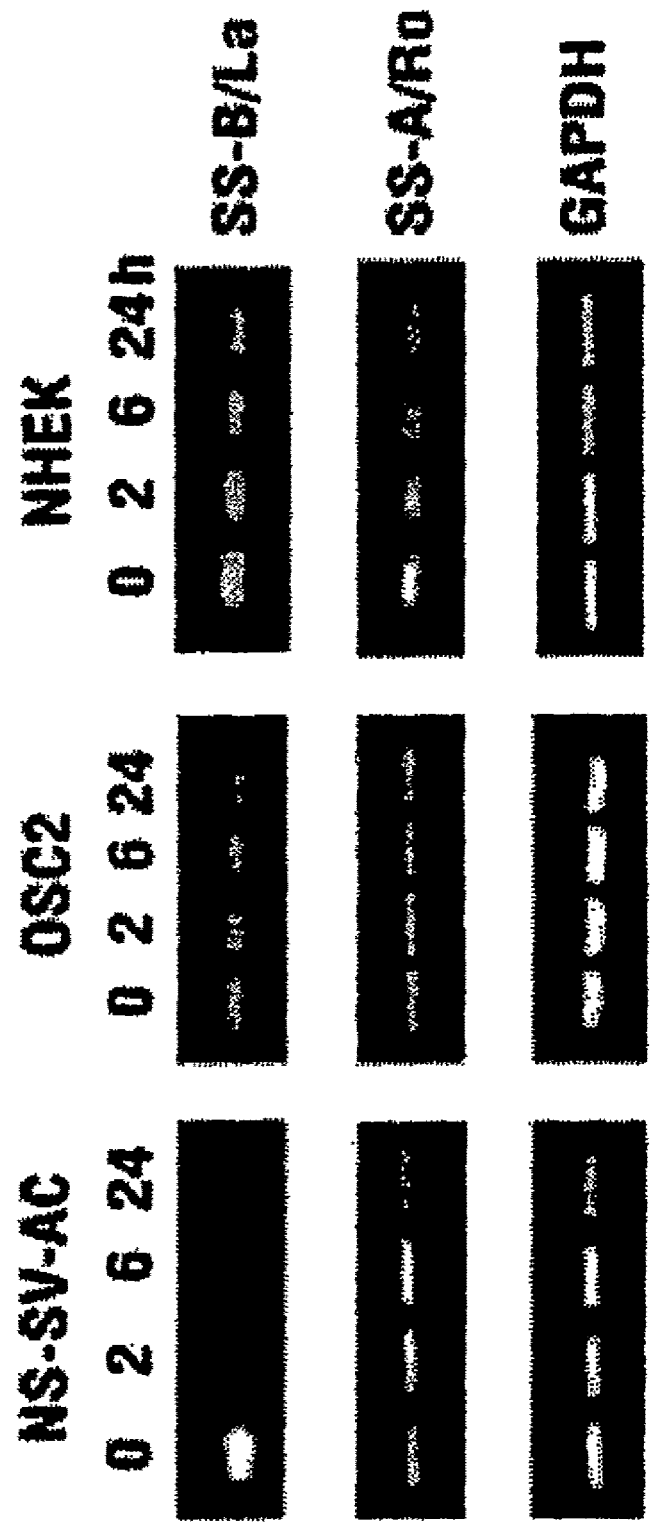
FIG. 1 shows a gel indicating mRNA levels of SS-B/La and SS-A/Ro in normal, immortalized, and tumor cells treated with (−)-epigallocatechin-3-gallate.

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting.

Throughout this disclosure, various publications, patents and published patent specifications are referenced. Where permissible, the disclosures of these publications, patents and published patent specifications are hereby incorporated by reference in their entirety into the present disclosure to more fully describe the state of the art.

To facilitate understanding of the disclosure, the following definitions are provided:

As used herein, the singular forms "a," "an," and "the" include plural referents unless the context clearly dictates otherwise. Thus, for example, reference to "a factor" refers to one or mixtures of factors, and reference to "the method of treatment" includes reference to equivalent steps and methods known to those skilled in the art, and so forth.

The term "autoantigen" refers to an antigen produced by an organism and recognized by the organism's immune system. Representative autoantigens include, but are not limited to those listed in Table 1.

The term "autoimmune disease or disorder" refers to conditions caused by an immune response against the body's own tissues or cells. Representative autoimmune disorders include, but are not limited to Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, scleroderma, psoriasis, xerostomia, and xeropthalmia.

The term "cell" refers to a membrane-bound biological unit capable of replication or division.

The term "Green Tea Polyphenols or GTP" refers to polyphenolic compounds present in the leaves of *Carmellia sinensis*. Green tea polyphenols include, but are not limited to (−)-epicatechin (EC), (−)-epigallocatechin (EGC), (−)-epicatechin-3-gallate (ECF), (−)-epigallocatechin-3-gallate (ECGC), proanthocyanidins, enantiomers thereof, epimers thereof isomers thereof, combinations thereof, and prodrugs thereof.

The term "host" refers to a living organism, including but not limited to a mammal such as a primate, and in particular a human.

The term "isolated," when used to describe the various compositions disclosed herein, means a substance that has been identified and separated and/or recovered from a component of its natural environment. For example an isolated polypeptide or polynucleotide is free of association with at least one component with which it is naturally associated. Contaminant components of its natural environment are materials that would typically interfere with diagnostic or therapeutic uses for the polypeptide or polynucleotide and may include enzymes, and other proteinaceous or non-proteinaceous solutes. An isolated substance includes the substance in situ within recombinant cells. Ordinarily, however, an isolated substance will be prepared by at least one purification step.

The term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

The term "pharmaceutically acceptable carrier" refers to a carrier or diluent that does not cause significant irritation to an organism and does not abrogate the biological activity and properties of the administered compound.

The term "pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the green tea polyphenols described herein, or a pharmaceutically acceptable salts thereof, with other chemical components, such as physiologically acceptable carriers and excipients. The purpose of a pharmaceutical composition is to facilitate administration of a compound to an organism.

The term "prodrug" refers to an agent, including nucleic acids and proteins, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm, Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of [beta]-Lactam antibiotics, Pharm. Biotech. 11,:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3): 183-209; Browne (1997). Fosphenyloin (Cerebyx), Clin. Neuropharmacol. 20(1): 1-12; Bundgaard (1979). Bioreversible derivatization of drugs— principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr Drug Metab., l(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4).265-87.

The term "treating or treatment" refers to alleviating, reducing, or inhibiting one or more symptoms or physiological aspects of a disease, disorder, syndrome, or condition.

2. Green Tea Compositions

One embodiment provides a composition having one or more green tea polyphenols, in particular (–)-epigallocatechin-3-gallate, a pharmaceutically acceptable salt, prodrug, or derivative thereof, in an amount effective to modulate expression of one or more autoantigens in a host compared to a control. Modulate means to increase, decrease, reduce, or inhibit expression of an autoantigen in a host or cell. Experimental controls or control groups are known in the art. Generally, the effect of the green tea polyphenol composition on the downregulation, inhibition, or modulation of an autoantigen can be compared to the effect of the composition without the green tea polyphenol on the down regulation, inhibition, or modulation of an autoantigen. Representative hosts include mammals such as humans.

A derivative or variant of a green tea polyphenol includes green tea polyphenols having chemical modifications to increase solubility or bioavailability in a host. These chemical modifications include the addition of chemical groups having a charge under physiological conditions as well as the conjugation of the green tea polyphenol to other biological moieties such as polypeptides, carbohydrates, lipids, or a combination thereof.

The disclosed green tea polyphenol composition can decrease or inhibit the expression of an autoantigen in any cell expressing an autoantigen or capable of expressing an autoantigen. Representative cells include, but are not limited to a primary epidermal keratinocyte, a salivary gland cell, or a lacrimal gland cell.

Autoantigens include, but are not limited to anti-nuclear autoantibodies such as SS-A/Ro, SS-B/La, centromere protein (CNEP) A, B, C, dsDNA, polymyositis-scleroderma (PM-scl), RNA polymerases, poly(ADP)ribose polymerase (PARP), uridine rich 1 small nuclear ribonucleoprotein (U1 snRNP), Smith antigen (Sm), ribosomal-P, histidyl t-RNA synthase (Jo-1), and DNA topoisomerase 1 (Scl-70) as well as those listed in Table 1.

Another embodiment provides a pharmaceutical composition including one or more green tea polyphenols in combination with a pharmaceutically acceptable carrier, diluent, or excipient. The one or more green tea polyphenols are in an amount modulate the expression of an autoantigen in a host. In some embodiments, the one or more green tea polyphenols are in an amount effective to inhibit, reduce, or decrease the expression of two or more autoantigens in a host. In other embodiments, the active ingredient in the composition consists essentially of (−)-e[rho]igallocatechin-3-gallate, a pharmaceutically acceptable salt or prodrug thereof. The active ingredient can be in the form a single optical isomer. Typically, one optical isomer will be present in greater than 85%, 90%, 95%, or 99% by weight compared to the other optical isomer. It will be appreciated that the composition can also include at least one additional active ingredient, for example a second therapeutic. Additional description of the disclosed pharmaceutical compositions is provided below.

3. Methods of Use

One embodiment provides a method for modulating expression of one or more autoantigens in a cell or host by contacting the cell or host with a green tea polyphenol composition. The green tea polyphenol composition includes an amount of one or more green tea polyphenols, pharmaceutically acceptable salts, prodrugs, or derivatives thereof in an amount effective to modulate the expression of an autoantigen. The expression of the autoantigen can be increased or decreased as compared to a control. The modulation of autoantigen expression can be at the transcriptional or translational stage. For example, the amount of mRNA encoding one or more autoantigens can be reduced or increased in cells contacted with a green tea polyphenol composition relative to a control. Alternatively, the amount of protein corresponding to an autoantigen can be increased or reduced in cells contacted with the disclosed green tea polyphenol compositions.

Another embodiment provides a method for treating an autoimmune disease by administering to a host an amount of one or more green tea polyphenols effective to reduce, inhibit, or decrease the expression of an autoantigen relative to a control. Representative autoimmune diseases include, but are not limited to Hahimoto's thyroiditis, pernicious anemia, Addison's disease, type I diabetes, rheumatoid arthritis, systemic lupus erythematosus (SLE), dermatomyositis, Sjogren's syndrome (SS), lupus erythematosus, multiple sclerosis, myasthenia gravis, Reiter's syndrome, Grave's disease, scleroderma, psoriasis, xerostomia, and xeropthlmia. Both SLE and SS are characterized by the production of autoantibodies that have been implicated in the pathogenic effects on tissues. To date, a large number of autoantigens have been identified in SLE. Sera from lupus patients often have high titers of anti-nuclear autoantibodies (ANAs) that target components of the nucleus (Sawalha and Harley, (2004) Curr Opin Rheumatol. 16(5):534-40). These ANAs include SS-A/Ro, SS-B/La, centromere protein (CNEP) A, B, C, dsDNA, polymyositis-scleroderma (PM-scl), RNA polymerases, [rho]oly(ADP)ribose polymerase (PARP), uridine rich 1 small nuclear ribonucleoprotein (U1 snRNP), Smith antigen (Sm), ribosomal-P, histidyl t-RNA synthase (Jo-1), and DNA topoisomerase 1 (Scl-70) (Reeves, G. E. (2004) Intern Med J. 34(6):338-7). ANAs are also found in about 70% of patients with SS, and autoantibodies against SS-A/Ro and SS-B/La are found in about 95% and 87% of primary SS patients, respectively (Rehman H. U. (2003) Yonsei Med J. 44(6):947-54). Elevated levels of SS-A/Ro and SS B/La mRNA were found in the salivary tissues of SS patients with xerostomia (Bolstad A. I., et al. (2003) Arthritis Rheum 48:174-85). Lupus-associated autoantigens also include golgins present in the Golgi apparatus and coilin proteins (Stinton, L. M. et al. (2004) Clin Immunol. 110(1):30-44).

The mechanism leading to presentation of autoantigens to the immune system is unknown. One mechanism that may initiate the autoimmune response is the translocation of nuclear autoantigens onto the cell membrane during apoptosis, where they are exposed to antigen-presenting cells such as macrophages and dendritic cells (Manganelli and Fietta, 2003). During apoptosis, autoantigens redistribute to form apoptotic bodies and blebs, where autoantigens such as SS-A/Ro, SS-B/La, Ku, poly(ADP)ribose polymerase (PARIP), fodrin, Golgins and nuclear mitotic apparatus protein (NuMA) are clustered as subcellular structures. An aberrant structure of these autoantigen complexes may contribute to the autoimmune response (Rosen and Casciola-Rosen, 2004). B cells can be stimulated to proliferate and produce autoantibodies by perturbations in the levels of cytokines. Although the exact role of autoantibodies in the pathogenesis SLE or SS remains unclear, it is thought they are involved directly in some of the clinical manifestations (Mamula et al, 1994).

Another embodiment provides a method for treating an autoimmune disease by administering to a host an amount of green tea polyphenol, for example ECGC, effective to downregulate the expression of autoantigens at the mRNA and/or protein levels, for example in different epithelial cell types. Still another embodiment provides a method for treating an autoimmune disease or disorder by administering to a host an amount of green tea polyphenol, for example ECGC, effective to reduce or inhibit expression of an autoantigen, reduce or inhibit apoptosis; and reduce or inhibit inflammation. The reduction in expression of an autoantigen, reduction of apoptosis, and the reduction of inflammation can be in any cell capable of expressing an autoantigen, for example in epithelial cells such as salivary gland cells, lacrimal gland cells, or primary epithelial keratinocyte.

Results from the Affymetrix gene expression analyses in Example 1 and Table 1 indicated that EGCG modulated the expression of a group of major autoantigens in NHEK, with several genes showing a 2-fold or more reduction in mRNA levels, in some cases after an initial increase. The various different patterns in the kinetics of change among different autoantigens suggests that different regulator mechanisms could be involved. (McArthur et al, 2002). Expression of SS-A/Ro 52 (which was not represented on the Affynatrix array) was shown to be reduced by ECCG at the mRNA and protein level in two different epithelial cell lines using RT-PCR and Western analyses. Similarly, microarray, RT-PCR and Western analyses demonstrated that EGCG reduced expression of SS-B/La. In contrast, the microarray analysis showed that SS-A/Ro 60 mRNA levels were not significantly altered by EGCG. Interestingly, oxidative stress induces cell surface expression of SS-A/Ro 52, but not SS-A/Ro 60 autoantigen on NHEK cells (Saegusa et al. 2002). Since green tea polyphenols inhibit the effects of oxidative stress on normal cells, this may be one mechanism by which EGCG reduces expression of autoantigens (Yamamotu et al, 2004). An inhibitory effect of EGCG on protein levels of four other autoantigens was demonstrated by Western analysis in NHEK and NS-SV-AC cells. The kinetics of reduction in protein levels differed somewhat between the autoantigens.

This could reflect regulation via different pathways, or differences in mRNA or protein stability, or in protein trafficking.

Figure 3:
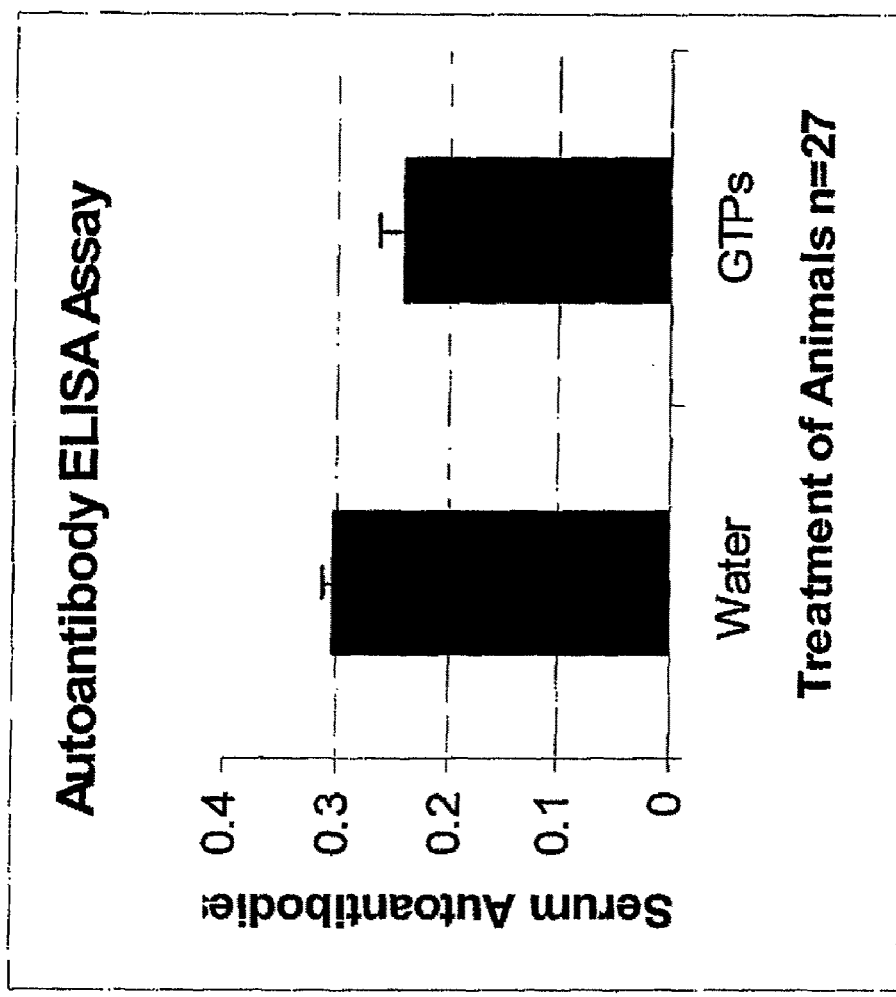
FIG. 3 shows mice treated with green tea polyphenols have reduced autoantibodies.
Figure 4:
FIG. 4A shows submandibular gland sections from control NOD mice.
FIG. 4B shows submandibular gland sections from NOD mice fed with green tea polyphenols.
Figure 4:
Figure 5:
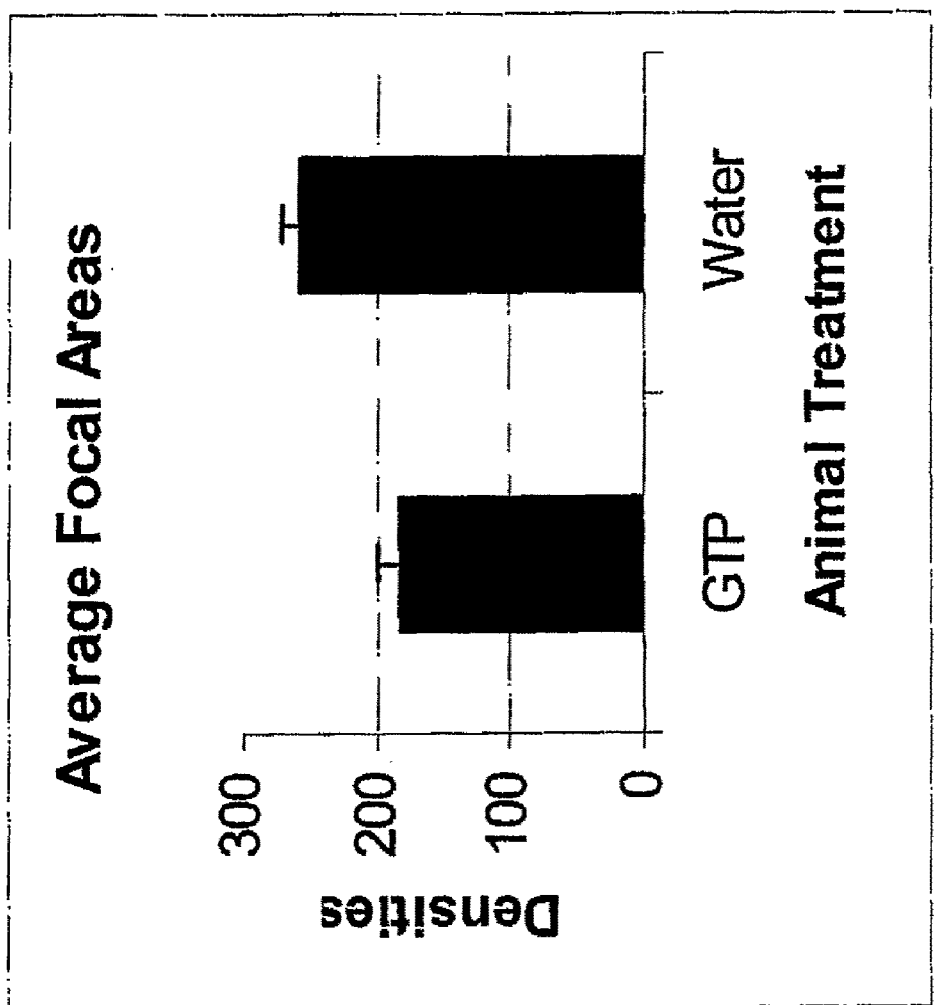
FIG. 5 shows a bar graph of the densities of the average focal areas in NOD mice fed green tea polyphenols compared to control mice.

Another embodiment provides a method for reducing or inhibiting SS-induced salivary gland destruction by administering to a host expressing one more symptoms of SS an amount of green tea polyphenols effective to reduce or inhibit one or more of apoptosis, autoantigen gene expression, or cytokine production. Examples 4 and 5 show a significant reduction of serum total autoantibody levels in GTP-treated NOD animals, compared with the untreated control NOD animals (FIG. 3). The NOD mouse is a known model for SS. Similarly, the size of lymphocytic infiltrate foci was also reduced after GTP treatment (FIGS. 4 and 5). Thus, another embodiment provides a method for reducing lymphocytic infiltration of salivary glands by administering to a host an amount of green tea polyphenols, for example ECGC, effective to reduce or inhibit the expression of an autoantigen.

The disclosed in vivo evidence indicates that GTPs have a beneficial effect against autoimmune responses in the NOD mouse. Green tea consumption by humans leads to an increase of secreted salivary GTPs, in a concentration range (50+µM) 10 times higher than the serum levels (Yang et al, 1999). Oral exposure to GTPs in this mouse model also results in elevation of salivary GTPs to protective concentrations. The GTP-treated group also had an average one week delay in the onset of autoimmune diabetes, and while all of the 15 GTP-fed NOD mice survived the 3-week disease progression period, two untreated control mice died during this period.

Although the size of the foci showed a significant difference between the two groups, the focal scores based on human diagnostic criteria did not differ. This could be due to species differences or more subtle differences between human SS and the NOD mouse model. A further possibility is that the time of onset of GTP treatment (9 weeks of age) might be relatively late with respect to the initial phases of the process of gland damage. NOD-scid congenic mice (that lack functional lymphocytes) do not develop sialadenitis (or diabetes). However, they do show dysfunction in expression of biochemical markers of salivary gland differentiation such as amylase and parotid secretory protein (PSP). These data are consistent with a model for SS in which there is an initial phase, during which dysregulation of glandular homeostasis triggers the disease, followed by an immune cell-mediated phase that leads to a loss of secretory function (Cha et al, 2002).

Still another embodiment provides a method for reducing or inhibiting autoimmune destruction of cells expressing an autoantigen by contacting the cells with an amount of green tea polyphenols, for example ECGC, effective to activate the p38 pathway in the cells.

The multiple MAPK signal transduction pathways are involved in the control of diverse cellular events including proliferation, differentiation and apoptosis. Gene expression in salivary epithelial cells is regulated, in part, via the Raf/MEK/MAPK pathway (Slomiany and Slomiany, 2003, Li et al, 1997). It was found that Raf-1 kinase-induced down-regulation of a sodium channel was blocked by the MEK inhibitor PD98059, suggesting that the ERK pathway is involved in the signal transduction (Zentner et al, 1998). The acinar cells respond to nitric oxide (NO), an inflammation-related signaling molecule, by the pathways regulated by ERK and p38 (Slomiany and Slomiany, 2002a). The p38 MAPK pathway is important in transducing stress signals, and p38 MAPK is strongly and rapidly activated by stresses and inflammatory cytokines (Dent et al, 2003). Recently, it was suggested that inhibition of LP S-stimulated iNOS and COX-2 expression and reduced NO release were by a mechanism involving p38 (Brautigam et al, 2005). SS patients show activated forms of p38 and JNK in infiltrating mononuclear cells (Nakamura et al, 1999). Protein kinases downstream of p38 can activate transcription factors such as activating transcription factor-2 (ATF-2) and growth and DNA damage (GADD)-153 transcription factor. The p38 MAPK family consists of at least 4 isoforms. The specificity of the isoforms activated depends on the cell type, and the nature and strength of the signals (Morin and Huot, 2004). Importantly, the cellular response to p38 MAPK activation is highly cell type dependent: it can induce apoptosis, growth arrest, or differentiation (Slomiany and Slomiany, 2002, Dent et al, 2003, Morin and Huot, 2004).

Figure 7:
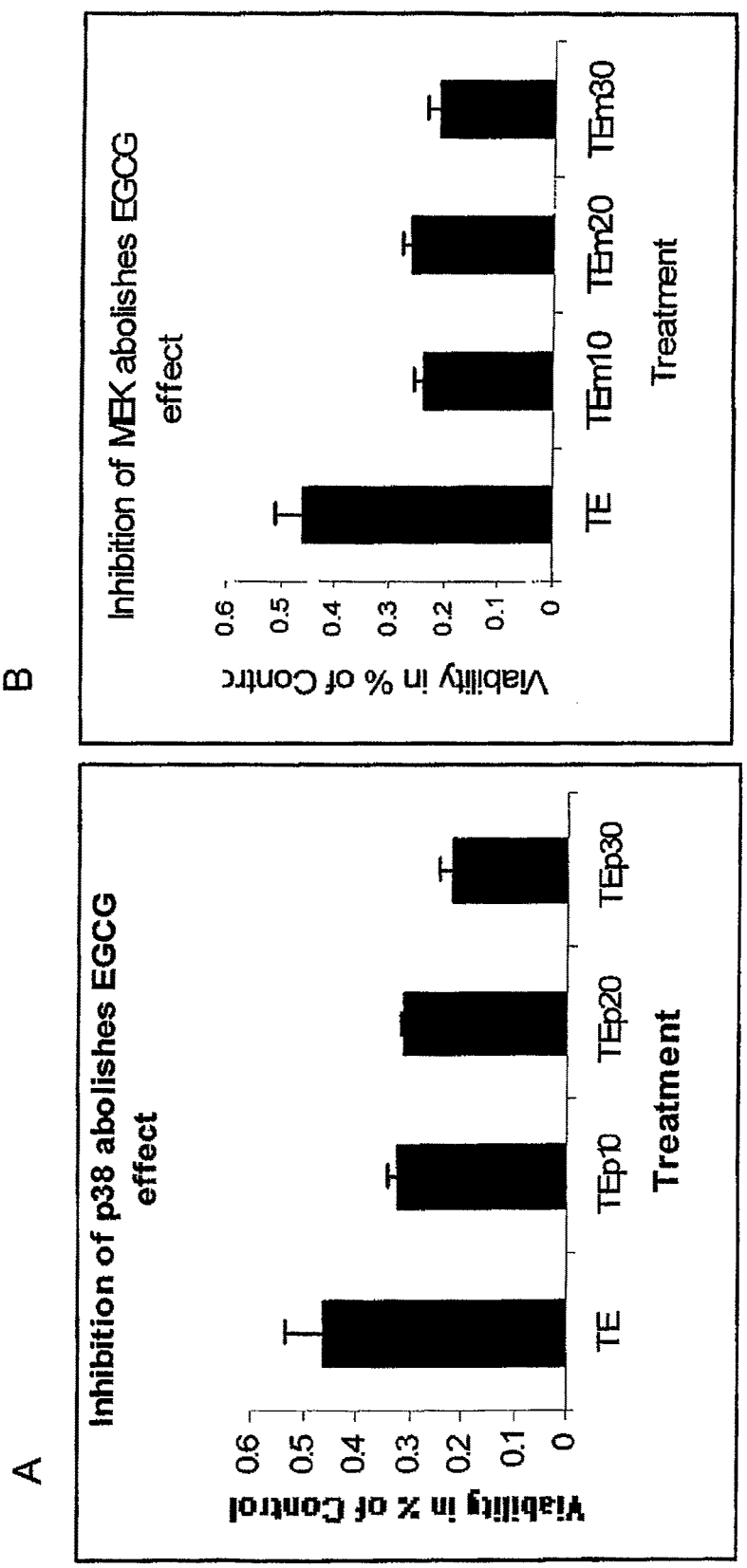
FIG. 7A shows a bar graph of cell viability indicating that inhibition of p38 abolishes EGCG protection.
FIG. 7B shows a bar graph of cell viability indicating that inhibition of MEK abolishes the EGCG effect.
Figure 8:
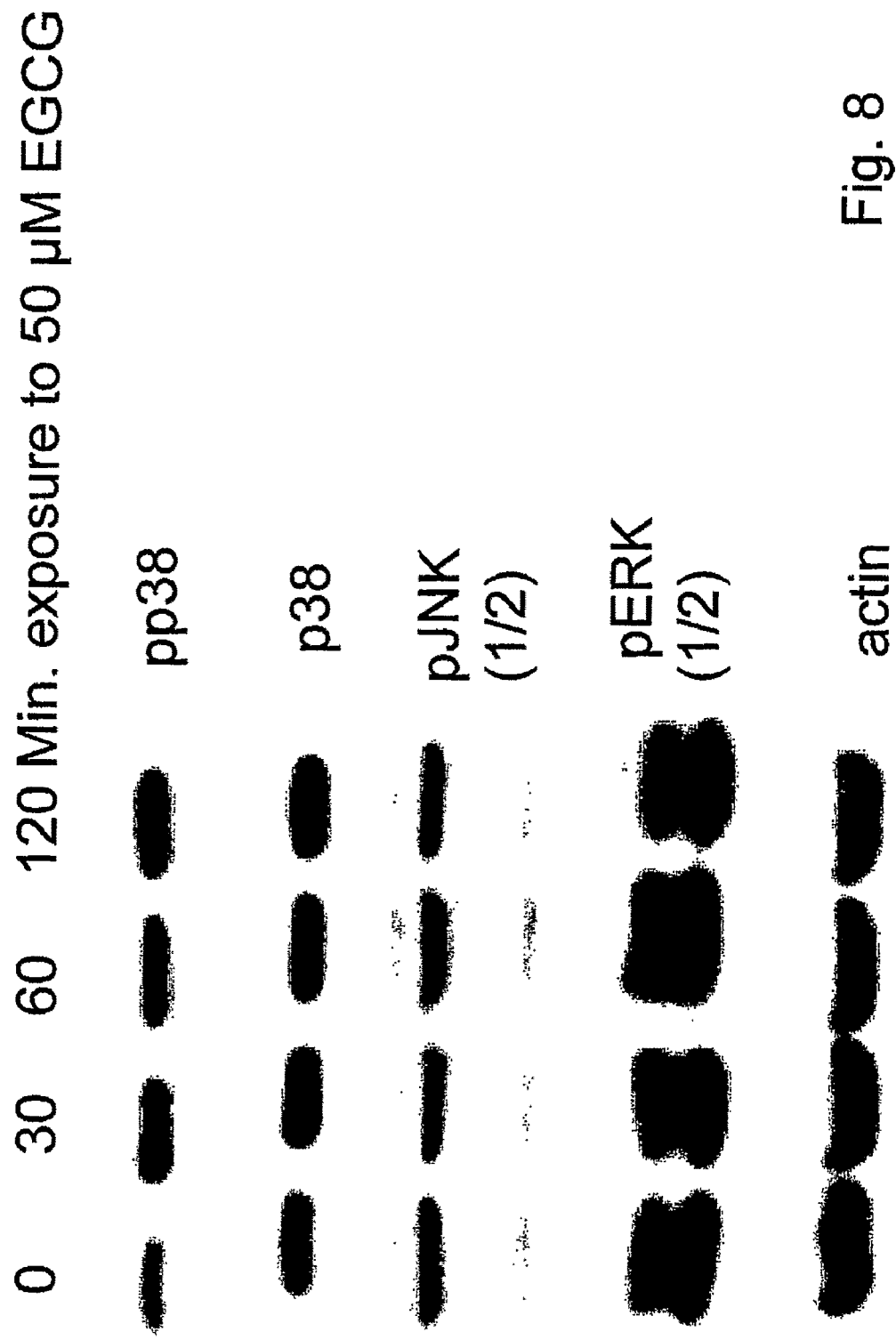
FIG. 8 shows an autoradiograph indicating that p38 is rapidly and specifically phosphorylated within 30 min in acinar cell-derived NS-SV-AC cells contacted with EGCG.

It has been discovered that EGCG induced the activation of p38 by phosphorylation in a dose dependent manner. p38 is rapidly and specifically phosphorylated within 30 min in acinar cell-derived NS-SV-AC cells by EGCG, while levels pJNK and pFRK were relatively stable (FIG. 8). Further, when NS-SV-AC cells were pre-treated with a specific inhibitor of p38, EGCG failed to protect these cells from TNF-α-induced cytotoxicity (FIG. 7A). An inhibitor of MEK, a MAPK upstream of p38, also blocked EGCG protection (FIG. 7B). Taken together, these results implicate the p38/MAPK pathway in mediation of some of the beneficial effects of GTPs on cell-based mechanisms of disease in SS-affected salivary glands. Accordingly, another embodiment provides a method for treating an autoimmune disorder by administering to a host an activator of the p38/MAPK pathway, in particular a green tea polyphenol compound.

Still another embodiment provides a method for treating xerostomia by administering to a host one or more green tea polyphenols in an amount effective to decrease expression of one or more autoantigens in one or more salivary gland cells of the host. Reducing the expression of an autoantigen in the salivary gland cell can reduce the autoimmune destruction of the salivary gland cell.

Another embodiment provides a method for treating xerophthalmia by administering to a host one or more green tea polyphenols in an amount effective to decrease expression of one or more autoantigens in one or more of the host's lacrimal gland cells. Reducing the expression of an autoantigen can prevent destruction of lacrimal gland cells.

Still another embodiment provides a method for treating psoriasis by administering to a host one or more green tea polyphenols in an amount effective to decrease expression of one or more autoantigens in one or more epidermal cells of the host. Reducing the expression of an autoantigen can prevent autoimmune destruction of epidermal cells.

Another embodiment provides use of a green tea polyphenol in the manufacture of a medicament for the treatment of an autoimmune disease, for example SS, psoriasis, xerophthalmia, or xerophthalmia.

4. Combination Therapy

The disclosed green tea polyphenol compositions can be used in combination or alternation with one or more additional therapies. Representative additional therapies that can be used with the disclosed compositions include, but are not limited to non-steroidal anti-inflammatory drugs, antimalarial drugs, corticosteroids, immunosuppressants, antioxidants, antibodies against T-cells or TNF-[alpha], and combinations thereof. Suitable non-steroidal anti-inflammatory drugs include ibuprofen, naproxen, indomethacin, celecoxib or other COX-2 inhibitors, rofecoxib, and combinations thereof. Treatment for psoriasis includes PUVA (UV light plus psorialin). Exemplary antimalarials include hydroxychloroquine. Representative corticosteroids include prednisone, prednisolone, and combinations thereof. Suitable immunosuppressants include azathioprine, methotrexate, cyclosporine, cyclophosphamide, leflunomide, mycophenolate, and combinations thereof. Additionally, herb al extracts, nutraceuticals, vitamins or combinations thereof can be used with or in addition to the disclosed compositions.

5. Pharmaceutical Compositions

Another embodiment provides pharmaceutical compositions and dosage forms which include a pharmaceutically acceptable salt of one or more green tea polyphenols, in particular, (–)-epigallocatechin-3-gallate or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical unit dosage forms of green tea polyphenols are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the green tea polyphenols of the disclosure will typically vary depending on their use. A parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient, for example a green tea polyphenol, will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of green tea polyphenol in a dosage form may differ depending on factors such as, but not limited to, the route by which it is to be administered to patients. However, typical dosage forms of the compounds of the disclosure include a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Topical dosage forms of the disclosure include, but are not limited to, creams, lotions, ointments, gels, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 11th Ed., Mack Publishing, Easton, Pa. (1990); and Introduction to Pharmaceutical Dosage Forms, 4th Ed., Lea & Febiger, Philadelphia, Pa.

(1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the green tea polyphenols of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a green tea polyphenol of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a tight junction modulator can be used to further adjust the properties of the resulting composition.

The disclosed green tea polyphenol compositions can also be formulated as extended or delayed release formulations, Extended and delayed release formulations for various active ingredients are known in the art, for example by encapsulation.

6. Encapsulation of Green Tea Polyphenols

In another embodiment, the green tea polyphenols can be incorporated into a polymeric component by encapsulation in a microcapsule. The microcapsule can be fabricated from a material different from that of the bulk of the carrier, coating, or matrix. Suitable microcapsules are those which are fabricated from a material that undergoes erosion in the host or those which are fabricated such that they allow the green tea polyphenol to diffuse out of the microcapsule. Such microcapsules can be used to provide for the controlled release of the encapsulated green tea polyphenol from the microcapsules.

Numerous methods are known for preparing microparticles of any particular size range. In the various delivery vehicles of the present invention, the microparticle sizes may range from about 0.2 µm up to about 100 µm. Synthetic methods for gel microparticles, or for microparticles from molten materials are known, and include polymerization in emulsion, in sprayed drops, and in separated phases. For solid materials or preformed gels, known methods include wet or dry milling or grinding, pulverization, size separation by air jet, sieve, and the like.

Microparticles can be fabricated from different polymers using a variety of different methods known to those skilled in the art. Exemplary methods include those set forth below detailing the preparation of polylactic acid and other microparticles. Polylactic acid microparticles are preferably fabricated using one of three methods: solvent evaporation, as described by Mathiowitz, et al. (1990) J. Scanning Microscopy 4:329; Beck, et al. (1979) Fertil. Steril. 31: 545; and Benita, et al. (1984) J. Pharm. Sci. 73: 1721; hot-melt microencapsulation, as described by Mathiowitz, et al., Reactive Polymers 6: 275 (1987); and spray drying. Exemplary methods for preparing microencapsulated bioactive materials are set forth below.

In the solvent evaporation method, the microcapsule polymer is dissolved in a volatile organic solvent, such as methylene chloride. The green tea polyphenol (either soluble or dispersed as fine particles) is added to the solution, and the mixture is suspended in an aqueous solution that contains a surface active agent such as poly(vinyl alcohol). The resulting emulsion is stirred until most of the organic solvent has evaporated, leaving solid microparticles. The solution is loaded with the green tea polyphenol and suspended in vigorously stirred distilled water containing poly(vinyl alcohol) (Sigma). After a period of stirring, the organic solvent evaporates from the polymer, and the resulting microparticles are washed with water and dried overnight in a lyophilizer. Microparticles with different sizes (1-1000 µm) and morphologies can be obtained by this method. This method is useful for relatively stable polymers like polyesters and polystyrene. Labile polymers such as polyanhydrides, may degrade during the fabrication process due to the presence of water. For these polymers, the following two methods, which are performed in completely anhydrous organic solvents, are preferably used.

In the hot melt encapsulation method, the polymer is first melted and then mixed with the solid particles of biologically active material that have preferably been sieved to less than 50 microns. The mixture is suspended in a non-miscible solvent (like silicon oil) and, with continuous stirring, heated to about 5. degree. C. above the melting point of the polymer. Once the emulsion is stabilized, it is cooled until the polymer particles solidify. The resulting microparticles are washed by decantation with a solvent such as petroleum ether to give a free-flowing powder. Microparticles with sizes ranging from about 1 to about 1000 microns are obtained with this method.

The external surfaces of capsules prepared with this technique are usually smooth and dense. This procedure is preferably used to prepare microparticles made of polyesters and polyanhydrides.

The solvent removal technique is preferred for polyanhydrides. In this method, the green tea polyphenol is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range from about 1 to about 300 µm can be obtained by this procedure. The external morphology of spheres produced with this technique is highly dependent on the type of polymer spray drying, the polymer is dissolved in methylene chloride. A known amount of the green tea polyphenol is suspended or co-dissolved in the polymer solution. The solution or the dispersion is then spray-dried. Microparticles ranging between about 1 to about 10 µm are obtained with a morphology which depends on the type of polymer used.

In one embodiment, the green tea polyphenol is encapsulated in microcapsules that comprise a sodium alginate envelope. Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for about twenty to thirty minutes in order to allow sufficient time for gelation to occur. Microparticle size is controlled by using various size extruders or varying either the nitrogen gas or polymer solution flow rates.

Liposomes can aid in the delivery of the green tea polyphenol to a particular tissue and also can increase the half-life of green tea polyphenol. Liposomes are commercially available from a variety of suppliers. Alternatively, liposomes can be prepared according to methods known to those skilled in the art, for example, as described in Eppstein et al., U.S. Pat. No. 4,522,811. In general, liposomes are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., Ann. Rev. Biophys. Bioeng. 9: 467 (1980); and U.S. Pat. Nos. 4,235,871, 4,501,728, 4,837,028, and 5,019,369. In one embodiment the liposomes encapsulating the green tea polyphenol comprise a ligand molecule that can target the liposome to a particular cell or tissue at or near the site of psoriasis. Ligands which bind to receptors prevalent in eplithelial tissue, such as monoclonal antibodies that bind to epithelial tissue, In one embodiment, the liposomes encapsulating the green tea polyphenols of the present disclosure are modified so as to avoid clearance by the mononuclear macrophage and reticuloendothelial systems, for example by having opsonization-inhibition moieties bound to the surface of the structure. In one embodiment, a liposome can comprise both opsonization-inhibition moieties and a ligand. Opsonization-inhibiting moieties for use in preparing the liposomes in one embodiment are large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016. Liposomes modified with opsonization-inhibition moieties thus remain in the circulation much longer than unmodified liposomes. For this reason, such liposomes are sometimes called "stealth" liposomes. Stealth liposomes are known to accumulate in tissues fed by porous or "leaky" microvasculature. In addition, the reduced uptake by the RES lowers the toxicity of stealth liposomes by preventing significant accumulation in the liver and spleen.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GMI. Copolymers of PEG, methoxy PEG, or methoxy PPG, or derivatives thereof; are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; laminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes," The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH3 and a solvent mixture such as tetrahydrofuran and water in a 30:12 ratio at 60° C.

The disclosed microparticles and liposomes and methods of preparing microparticles and liposomes are offered by way of example and are not intended to define the scope of microparticles or liposomes of use in the present disclosure. It will be apparent to those of skill in the art that an array of microparticles or liposomes, fabricated by different methods, are of use in the present invention.

Materials and Methods

Chemicals and antibodies: EGCG was purchased from Sigma-Aldrich (St. Louis, Mo.). Anti-human CENP-C (H-300) Rabbit polyclonal antibody, Anti-human 52 KD Ro/SSA (D-12) mouse monoclonal antibody, anti-human PARP (F-2) mouse monoclonal antibody, anti-human p38, pp 38, pJNK and pERK antibodies, and anti-human actin (1-19) goat polyclonal antibody were purchased from Santa Cruz Biotechnology, Santa Cruz, Calif. The anti-human coilin mouse monoclonal antibody was obtained from By Transduction Laboratories, San Jose, Calif. The anti-human Golgin-67 rabbit polyclonal antibody was a kind gift from Dr. Don Fujita, University of Calgary, Canada. The anti-human La/SSB mouse monoclonal antibody was purchased from Immunovision Diagnostics Inc., Springdale, Ark. The mouse Anti-Nuclear Antibodies (ANA) ELISA Kit was purchased from Alpha Diagnostic International, Inc. San Antonio, Tex. Specific inhibitors for p38 (SB 203580), JNK (Sp600125) and ERK (PD 98059) were supplied by EMD Bioscience, Inc., San Diego, Calif. The 70% GTPs are provided by Zhejinag Cereals, Oils & Foodstuffs Imp/Exp Co., Ltd, China, which contain 40% EGCG, 13% ECG, 7.3% EGC, 3.2% EC, and 2.7% Caffeine. Animal treatment. The NOD mice were purchased from Jackson Laboratory. The NOD/LtJ strain develops spontaneous autoimmune symptoms that resemble human SS (Cha, S. et al. (2002) Crit. Rev Oral Biol Med. 13:4-16). The NOD mouse is an important model system that has provided clues to the cellular mechanisms involved in SS. Almost 50% of published animal studies for SS used this model during the past two years. This mouse strain develops a lymphocytic infiltration of exocrine tissues at 10-12 weeks of age, particularly in females, and was originally used as a model for type I diabetes. NOD-scid congenic mice (that lack functional lymphocytes) do not develop sialadenitis (or diabetes). However, they do show dysfunction in expression of biochemical markers of salivary gland differentiation such as amylase and parotid secretory protein (PSP). These data are consistent with a model of SS in which there is an initial phase during which dysregulation of glandular homeostasis triggers the disease, followed by an immune cell-mediated phase that leads to a loss of secretory function. All animal protocols in this study were approved by the Institutional Animal Care and Use Committee. Animals (two groups, 15 NOD mice/group) were allowed ad libitum access to either water or 0.2% GTPs starting at the $9^{th}$ week of age. After the onset of autoimmune disease (determined as diabetes, detected by Glucotest strips), each animal was allowed to progress with the disease for three weeks, and then euthanized (2 water-fed control mice died during this 3-week period). Blood was collected from each animal in the above described treatment groups by cardiac puncture immediately after euthanasia, and serum for ELISA assays was prepared by centrifugation of blood samples at 3000 rpm. The submandibular glands were dissected free of the sublingual gland and attached tissues for pathological analyses.

Determination of serum total autoantibodies: Samples from the two groups were examined by ELISA assays for anti-SS-associated autoantibodies using the Mouse Anti-Nuclear Antibodies (ANA) ELISA Kit (Cat #5200, Alpha Diagnostic International, Inc. San Antonio, Tex.) according to the manufacturer's instructions. This kit detects total ANA against ds-DNA, ss-DNA, histones, ribonucleoproteins (RNPs), SS-A, SS-B, SM antigens, Jo-1, and Scl-70. Samples were analyzed with blanks, positive and negative controls in 96-well plates by ELISA reaction, photo-detection using a VERSAmax Microplate Reader at 450 nm, and statistical analysis using two-tailed student t-test.

Immunohistochemistry: The submandibular glands from NOD mice were fixed in 10% neutral-buffered formalin, paraffin embedded, sectioned at 5 [mu]m, and stained with H&E by routine methods previously described (Hsu et al, 2005).

Pathology scoring of lymphocyte infiltration in the submandibular glands of NOD mice, We adopted the cumulative focus score (cFS) criteria recently published by Morbini et al. (101) for the assessment of salivary gland inflammatory infiltrates as a component of the diagnosis of Sjögren's syndrome (SS). Briefly, these criteria modify the American-European Consensus Group (Vitali et al, 2002) focus score (FS) criterion as a component of the diagnosis of SS by adopting a multilevel sectioning and evaluation of salivary gland tissues of suspected SS patients. This multilevel sampling improved the diagnostic accuracy of biopsies with a baseline FS between 1 and 2, which represents the critical cutoff in SS histopathological evaluation (Morbini et al, 2005). The cFS method assesses the number of chronic (lymphocytic) inflammatory cell infiltrates of at least 50 in a 10-HP (equivalent to 4 $mm^2$) light microscopy field repeated for a minimum of three different tissue section levels. The arithmetic average FS from all examined levels from a particular gland represents the cFS average for that gland. To examine differences in the size of foci above 50 cells, a quantitative analysis was performed using the BIOQUANT NOVA PRIME 6.75 software. One H&E-stained submandibular salivary gland section was selected at random for each of the animals in the two groups and images of areas containing foci were loaded into the software. The areas of lymphocyte infiltration foci were captured individually and measured quantitatively by the software as relative density units.

Cell lines: NHEK were purchased from Cambrex (East Ruthtrford, N.J.) and sub-cultured in KGM-2 provided by the manufacturer. Subculture of the NHEK was performed by detaching the cells in 0.25% trypsin, and transferring into new tissue culture flasks. The immortalized human salivary gland acinar cells NS-SV-AC have been previously described (Azuma M. et al. (1993) Lab Invest. 69(1):24-42). These cells were selected following transfection of origin-defective SV40 mutant DNA and maintained in KOM-2 medium, they were kindly provided by Dr. Masayuki Azuma (Tokushima University School of Dentistry, Tokushima, Japan). Subculture of the cells was performed by detaching the cells in 2.5% trypsin, and transferring into new tissue culture flasks.

Cell treatment: ECCG was dissolved in cell culture media as a 50 mM stock immediately before use. Exponentially growing NS-SV-AC cells were incubated with 100 μM ECCG for various time periods in the growth media described above, and then were either extracted for total RNA or cell lysates prior to RT-PCR or Western blots.

Affymetrix Gene Array Analyses

The gene array experiment was performed at the Core Facility of Genomics of the Medical College of Georgia, according to the instructions of the manufacturer (Affymetrix, Santa Clara, Calif.). Briefly, NHEK and OSC2 cells treated with 100 μM EGCG for different time period were extracted for total RNA, the RNA was processed for probes and hybridized with a cDNA microarray (HuG133A, Affymetrix) which represents 22,283 human series. DNA chips were read with a Hewlett-Packard GeneArray Scanner at a resolution of 3 mm and were analyzed with the GeneSpring software (Silicon Genetics, Redwood City, Calif.). Details of this analysis will be published elsewhere (Hsu et al., manuscript in preparation).

Total RNA Extraction and Semi-Quantitative Reverse-Transcription PCR (KT-PCR)

Total RNA was extracted using an RNeasy total RNA isolation system (QIAGEN, Valentia, Calif.) RT reactions and PCR reactions were performed according to the manufacturer's protocol (Super Array Bioscience Corp). For amplification, the following pair of primers was used,

```
GAPDH:
Sense,
5'-TCCCATCACCATCTTCCA-3',          (SEQ ID NO. 1)

Antisense,
5'-CATCACGCCACACGAGTTTCC-3',        (SEQ ID NO: 2)

SS-A/Ro (469 bp):
sense
5'-GAACTGCTGCAGGAGGTGATAA-3',       (SEQ ID NO: 3)

Antisense
5'-GGCACATTCAGAGAAGGAGT-3',         (SEQ ID NO: 4)

SS-B/La (95 bp):
sense
5'-CCAAAATCTGTCATCAAATTGAGTATT-3', (SEQ ID NO: 5)

Antisense
5'-CCAGCCTTCATCCAGTTTTATCT-3',      (SEQ ID NO: 6)
```

Amplification was started by heating for 1.5 min at 94° C., followed by 30 cycles for 52 kD SSA/Ro. 25 cycles for GAPDH and 25 cycles for SSB/La, each cycle consisting of 15 second at 94° C., 30 seconds at 57.3° C., and 1 min at 72° C. A final extension was performed at 72° C. for 5 min prior to gel analysis.

Western blot. Cells were washed in ice-cold PBS and lysed for 20 min in RIPA buffer containing 1% (v/v) Nonidet P-40, 0.5% (w/v) sodium deoxycholate, 0.1% (w/v) SDS, 10 μg/ml leupeptin, 3 μg/ml aprotinin and 100 mM phenylmethylsulfonyl fluoride (PMSF). Samples of lysates containing the same amount of protein were loaded in each lane (we used 5-30μg, depending on the antibody used) and electrophoretically separated on a 12% SDS polyacrylamide gel. Following electrophoresis, proteins were transferred to a PVDF membrane (Immobilon™-P, Millipore Corporation, Bedford, Mass.). The membrane was blocked for 1 h with 5% (w/v) non-fat dry milk powder in PBST (0.1% Tween-20 in PBS) and then incubated for 1 h with primary antibody diluted in PBST/milk (Antibodies and dilutions: rabbit polyclonal JNK1/2, 1:000, mouse monoclonal pJNK1/2, 1:1000, rabbit polyclonal ERK, 1:2000, rabbit polyclonal p38, 1:1000, rabbit polyclonal pp 38, 1:1000 and goat polyclonal actin, 1:2000). The membrane was washed three times with PBST and incubated with peroxidase-conjugated, affinity-purified anti-rabbit IgG (Santa Cruz Biotechnology, Inc.) for 1 h. Following extensive washing, the reaction was developed by enhanced chemiluminescent staining using ECL Western blotting detection reagents (Amersham Pharmacia Biotech Inc., Piscataway, N.J.).

TNF-α cyotoxicity: NS-SV-AC cells (0.5×10<4> cells/well) were seeded in a 96-well microplate and either treated for 24 hr with EGCC as described above (or not treated in the control), in the presence of 100 ng/ml TNFα and 10 μg/ml cyclohexamide. After the treatments, viability was determined by the MTT assay. The cells in each well were washed with 200 μl of phosphate-buffered saline (PBS) and incubated with 100 μl of 2% (w/v) MTT in a solution of 0.05 M Tris-HCl (pH 7.6), 0.5 mM $MgCl_2$, 2.5 mM $CoCl_2$ and 0.25 M disodium succinate at 37° C. for 30 min. Cells were fixed by the addition of 100 μl of 4% (v/v) formalin in 0.2 M Tris-HCl (pH 7.6), and after a 5 min incubation at room temperature liquid was removed and the wells were allowed to dry. Each well was rinsed with 200 μl water and cells were solubilized by the addition of 100 μl of 6.35% (v/v) 0.1 N NaOH in DMSO. The colored formazan product was measured by a Thermo MAX micro plate reader (Molecular Devices Corp. Sunnyvale, Calif.) at a wavelength of 562 nm.

EXAMPLES

Example 1

Affymetrix Gene Array Analyses

Gene assays provide a valuable tool for studying the broad response of cells to agents, and we have used this approach to compare the differential effects of GTPP on gene expression in NHEK and human oral squamous carcinoma cells (Hsu, et al, manuscript in preparation). The results demonstrated that approximately 2100 genes were either up- or down-regulated by at least 2-fold in response to 100 uM EGCG in both cell types during the 24 hrs post-treatment. Examination of the relative NHEK mRNA levels of genes represented on the chip encoding autoantigens previously identified in SLE (Sherer et al., 2004) revealed a 2-fold or greater change in expression of a number of genes during the 24 hr post-treatment time course (Table 1). See also Hsu, S. et al. (2005) JPET 315:805-811, which is incorporated by reference in its entirety.

Several patterns of change were observed. For example, the nuclear autoantigen genes (RNA polymerase I and SS-B/La), a cytoskeletal autoantigen gene (alpha-fodrin) and a Golgi autoantigen gene (golgin-67) showed a general pattern of rapid (0.5-2 hr initiation) and persistent 2-fold or greater decrease in mRNA levels during the 24 hr period. Other genes showed an initial decrease during the first 2 hrs (e.g., centromere protein Cl, coilin), with levels returning to near normal by 24 hrs. Other autoantigen genes (e.g., nuclear antigen SPIOO and scleroderma autoantigen 1) showed a rapid initial increase (2-4-fold) followed by a 2-fold or greater decrease. Other genes (e.g., one of the arrayed Ku autoantigen genes) showed a transient initial increase, with levels returning to near normal. In contrast, other antoantigen genes did not show a significant change during the time course of the experiment. For example, 60 kDa SS-A/Ro did not decline significantly (52 kDa SS-A/Ro cDNA was not included in the gene array).

TABLE 2

Summary of gene array analysis of autoantigen gene expression. Analysis of the gene array dataset for EGCG-treated normal human epidermal keratinocytes (NHEK) cells demonstrates a general pattern of reduction in autoantigen gene expression.

| Affymetrix cDNA Array Symbols | Time 0, Cell Type NHEK normalized | Time 0.5, Cell Type NHEK normalized | Time 02, Cell Type NHEK normalized | Time 06, Cell Type NHEK normalized | Times 24, Cell Type NHEK normalized | Genes coding for autoantigens |
|---|---|---|---|---|---|---|
| 20473_at | 1 | 1.27 | 0.46 | 0.87 | 0.94 | centromere protein C1 |
| 203653_s_at | 1 | 0.49 | 0.54 | 0.60 | 0.79 | coilin |
| 203654_s_at | 1 | 1.11 | 0.78 | 0.62 | 0.79 | coilin |

TABLE 2-continued

Summary of gene array analysis of autoantigen gene expression. Analysis of the gene array dataset for EGCG-treated normal human epidermal keratinocytes (NHEK) cells demonstrates a general pattern of reduction in autoantigen gene expression.

| Affymetrix cDNA Array Symbols | Time 0, Cell Type NHEK normalized | Time 0.5, Cell Type NHEK normalized | Time 02, Cell Type NHEK normalized | Time 06, Cell Type NHEK normalized | Times 24, Cell Type NHEK normalized | Genes coding for autoantigens |
|---|---|---|---|---|---|---|
| 208797_s_at | 1 | 1.26 | 0.71 | 0.92 | 0.29 | golgin-67 |
| 208798_x_at | 1 | 0.81 | 0.46 | 0.32 | 0.31 | golgin-67 |
| 210425_x_at | 1 | 0.50 | 0.47 | 0.19 | 0.31 | golgin-67 |
| 213650_at | 1 | 0.24 | 0.61 | 0.69 | 0.72 | golgin-67 |
| 200792_at | 1 | 1.15 | 1.19 | 1.13 | 0.79 | thyroid autoantigen 70 kDa (Ku antigen) |
| 208642_s_at | 1 | 1.29 | 1.14 | 0.96 | 0.73 | Ku autoantigen, 80 kDa |
| 208643_s_at | 1 | 2.34 | 1.40 | 0.98 | 0.77 | Ku autoantigen, 80 kDa |
| 202692_s-at | 1 | 0.50 | 0.48 | 0.50 | 0.55 | RNA polymerase 1 |
| 208611_s_at | 1 | 0.41 | 0.75 | 0.56 | 0.42 | fodrin-α |
| 212071_s_at | 1 | 0.91 | 0.92 | 0.95 | 0.72 | spectrin-β non-erythrocyctic 1 |
| 215235_s_at | 1 | 0.49 | 0.97 | 0.75 | 0.71 | fodrin-α |
| 212852_s_at | 1 | 0.60 | 0.98 | 0.85 | 0.94 | 60 kDa, SS-A/Ro |
| 210438_x_at | 1 | 0.71 | 0.92 | 0.69 | 0.88 | 60 kDa, SS-A/Ro |
| 201139_s_at | 1 | 0.71 | 0.74 | 0.43 | 0.26 | SS-B/La |
| 201138_s_at | 1 | 0.84 | 0.88 | 0.57 | 0.27 | SS-B/La |
| 202863_at | 1 | 1.72 | 1.04 | 0.59 | 0.36 | Nuclear antigen SP100 |
| 202864_s_at | 1 | 3.12 | 1.21 | 0.64 | 0.08 | Nuclear antigen SP100 |
| 213226_at | 1 | 3.99 | 1.09 | 0.43 | 0.50 | Nuclear antigen SP100 75 kDa |
| 213226_at | 1 | 3.99 | 1.09 | 0.43 | 0.50 | scleroderma autoantigen 1, 75 kDa |

An additional mechanism by which EGCG modulation of gene expression could afford protection in autoimmune disorders might be by reduction in the expression of proinflammatory signaling molecules. Data show that there is a broad reduction in expression of pro-inflammatory genes. Table 3 shows the results for a number of improtant inflammation-related genes whose expression in NHEK is modulated by EGCG (the entire group is too large to display). These data show that EGCG can suppress the expression of many inflammatory factors. Importantly, the MAPK family member p38 is induced.

TABLE 3

Selected inflammatory gene expression detected from NHEK treated with 100 μM EGCG for indicated hours. Except p38 and IL8, all other genes were inhibited by EGCG. Numbers represent fold up/down at the time points indicated.

| Affymetrix symbols | Common Names | Time 0, Cell Type NHEK normalized | Time 0.5, Cell Type NHEK normalized | Time 02, Cell Type NHEK normalized | Time 06, Cell Type NHEK normalized | Times 24, Cell Type NHEK normalized |
|---|---|---|---|---|---|---|
| 205067_at | IL1B | 1 | 0.29 | 0.58 | 0.49 | 0.26 |
| 39402_at | IL1B | 1 | 0.29 | 0.48 | 0.40 | 0.27 |
| 210118_s_at | IL1A | 1 | 0.66 | 0.42 | 0.54 | 0.27 |
| 205290_s_at | BMP2 | 1 | 0.32 | 0.96 | 0.72 | 0.44 |
| 206295_at | IL18 | 1 | 0.33 | 0.65 | 0.70 | 0.65 |
| 206172_at | IL13RA2 | 1 | 0.33 | 0.74 | 0.81 | 0.55 |
| 21100_s_at | IL6ST | 1 | 0.34 | 0.28 | 0.99 | 0.61 |
| 209575_at | IL10RB | 1 | 0.43 | 0.63 | 0.76 | 0.38 |
| 205945_at | IL6R | 1 | 0.48 | 0.69 | 0.31 | 0.69 |
| 221085_at | TNFSF15 | 1 | 0.52 | 1.56 | 0.67 | 0.63 |
| 202727_s_at | IFNGR1 | 1 | 0.79 | 0.91 | 0.45 | 0.92 |
| 202859_x_at | IL8 | 1 | 6.02 | 9.55 | 9.99 | 9.93 |
| 21156_x_at | p38 | 1 | 2.32 | 1.46 | 1.62 | 2.51 |
| 202530_at | p38 | 1 | 2.51 | 1.09 | 0.63 | 1.17 |

Example 2

Semi-quantitative RT-PCR

The preliminary array analysis described above provided data suggesting that GTPP could alter the expression of some genes encoding autoantigens. To further test this possibility, three cell types, NHEK, NS-SV-AC (an SV40 immortalized cell line derived from human submandibular acinar cells) and OC2 cells (derived from an oral squamous cell carcinoma) were treated with 100 uM EGCG for different times. A semi-quantitative estimate of SS-A/Ro and SS-B/La mRNA levels was then obtained by RT-PCR during the exponential period of amplification. GAPDH was used as a housekeeping gene control. SS-B/La and ES-A/Ro 52 were selected because elevated mRNA levels (2-3 fold) of SS-A/RO 52 and SS-B/La are found in salivary tissues of SS patients (Bolstad A. I., et al. (2003) Arthritis Rheum 48:174-185), and autoantibodies against SS-A/Ro end SS-B/La are found in nearly all (about 95% and 87%, respectively) primary SS patients (Hahn: 1998). Consistent with the gene array data, SS-R/La message decreased progressively and substantially in both NHEK and NS-SV-AC cells (FIG. 1). The levels of SS-A/Ro (52 kd) mRNA also showed a reduction during treatment, although the effect was less pronounced than that seen for SS-B/La and was not prominent until 24 hrs. In OSC2 cells the reduction in SS-B/La mRNA was less pronounced and did not occur until 24 hrs of exposure, while SS-A/Ro mRNA showed little change. GAPDII also showed no marked decrease in these cells in response to EGCG, indicating the reduction in mRNA levels seen for SS-B/La and SS-A/Ro was not due to a generalized effect on the cells.

Example 3

Protein Levels of Autoantigens

Figure 2:
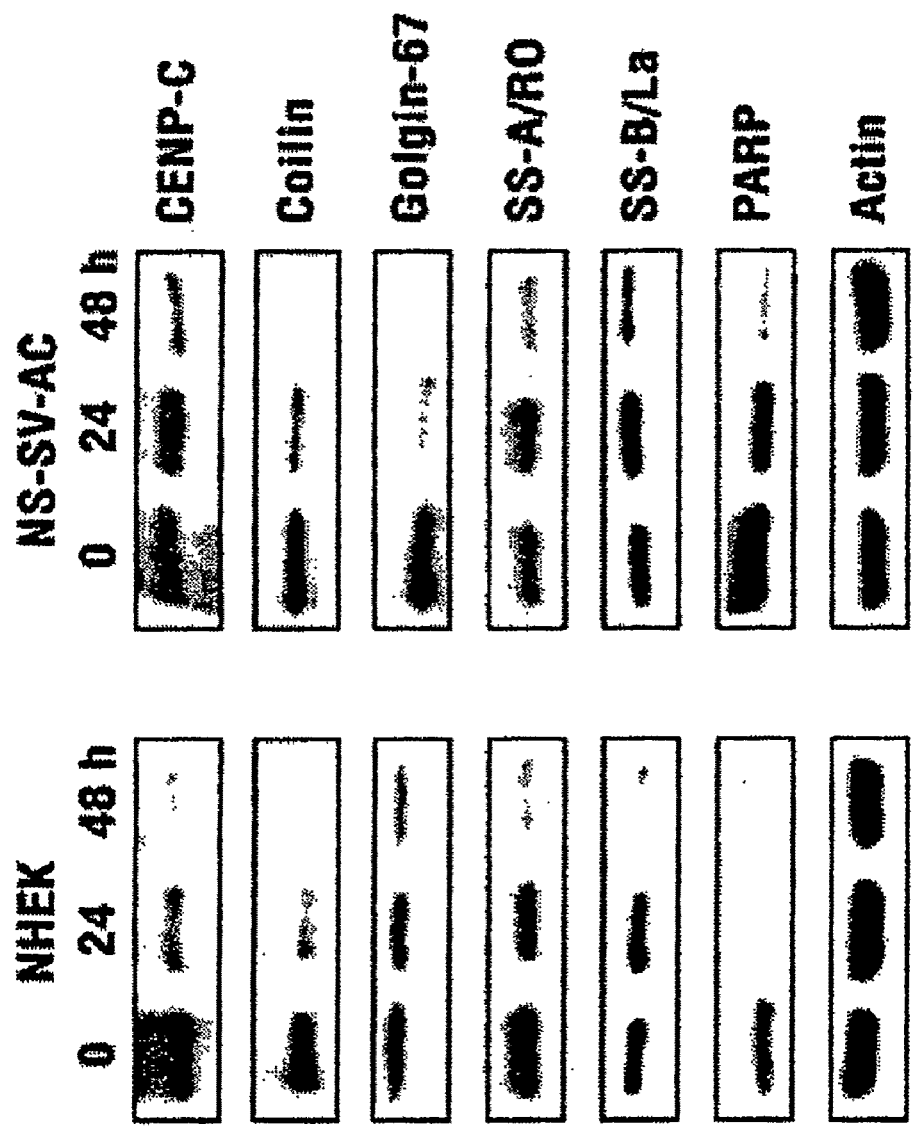
FIG. 2 shows Western blot results of autoantigen protein levels in (−)-epigallocatechin-3-gallate-treated NHEK and NS-SV-Ac cells.

To extend the mRNA data, the protein levels of 6 different autoantigens in NHEK and NS-SV-AC cells were determined by Western analysis following two treatments with 100 uM EGCSG at 24 and 48 hrs. As shown in FIG. 2, coilin and PARP protein levels were significantly reduced in both cell lines by 24 hrs, and were barely detectable after 48 hrs. CENP-C showed a similar trend, although the reduction was less pronounced. Neither SS-A/Ro 52 nor SS-B/La were significantly reduced in either cell line by 24 hrs, but were considerably reduced by 48 hrs. Golgin-67 was reduced in NS-SV-AC cells by 24 hrs, and barely detectable at 48 hrs. Golgin-67 was also reduced in NHEK cells, although the reduction was not as marked and was only observed at 48 hrs. Actin protein levels were unchanged by EGCG during the 48 hr treatment period.

Example 4

Serum Total Autoantibody ELISA

NOD mice were fed either water or water containing 0.2% GTPs for 3 weeks. Serum of 27 animals was analyzed: 15 from the GTP-water and 12 from the water-only group (two animals died, one animal was not able to collect serum in the latter group). There was a significant difference between the total serum antibody levels from the GTP-water group and water-only group. On average, the total ANA (against ds-DNA, ss-DNA, histones, ribonucleoproteins [RNPs], SS-A, SS-B, SM antigens, Jo-1, and Scl-70) in the GTP-water animal were approximately 20% lower than that of the water-only animals (FIG. 3). This result indicates that oral administration of GTPs significantly reduced the serum autoantibody levels (two-tailed student t-test, p=0.036, n=27).

Example 5

Analysis of Lymphocyte infiltration

The submandibular glands of each NOD animal were collected and the standardized scores for the inflammatory cell infiltrates were determined blindly, as described in the methods. FIG. 4 shows representative submandibular glands from a water-fed control (A) and a GTP/water-fed NOD mouse (3). Pathological focal scoring, using the cumulative focus score (cFS) criteria for SS diagnosis, demonstrated no significant difference in focal scores (i.e. the number of focal inflammatory cell aggregates containing 50 or more lymphocytes in each 4 mm$^2$ area) between the GTP-treated and untreated (water) controls. The average focal score was 2.125±1.13 for GTP-fed mice and 2.125±0.64 for control mice. However, inspection of the foci suggested potential differences in the focal areas between the groups, equivalent to differences in the total number of inflammatory cells/focus. For example, both animals shown in FIG. 4 received a focal score of 3, but the foci in the GTP-treated animal appear smaller (although for any one focal group this might just reflect an off-center cut through its volume). Quantitative analysis of the areas of lymphocyte infiltration foci in H&E-stained submandibular gland sections (FIG. 5, n=27 animals) demonstrated a statistically significant difference (p=0.006, two-tailed t-test, n=83 foci/group) between the groups in the number of inflammatory cells/infiltrate, with fewer cells in the salivary glands of GTPs/water-fed animals.

Example 6

Figure 6:
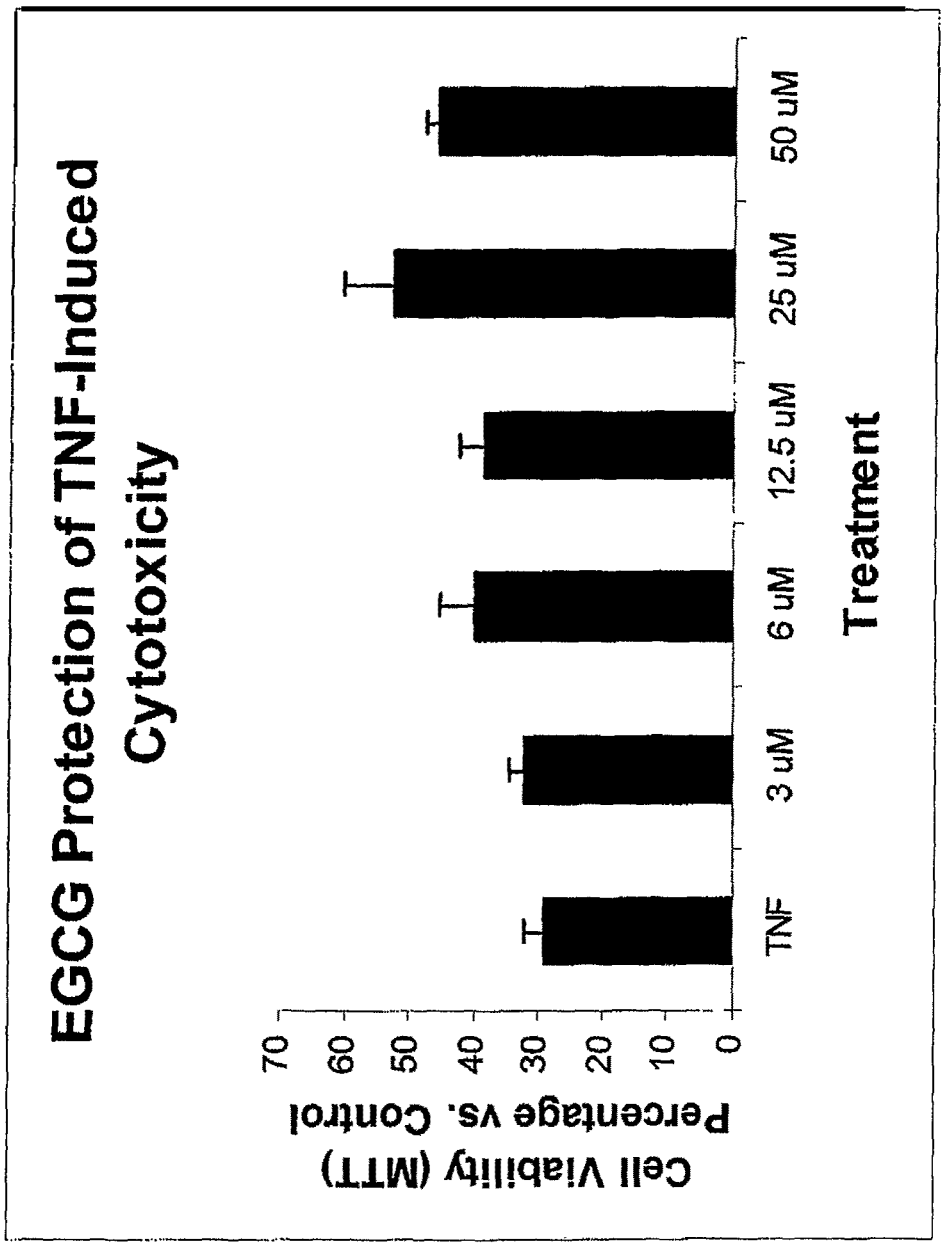
FIG. 6 shows a bar graph of cell viability indicating that ECGC protects cells against TNF-induced cytotoxicity.

Human Salivary Gland Acinar Cells are Protected from TNF-α-Induced Cytotoxicity by EGCG TNF-α, which is produced by inflammatory cells, is known to induce cytotoxicity in many cell types, and can be down-regulated by EGCG (Suganuma et al, 2000, Fujiki et al, 2000, Fujiki et al, 2003). Therefore, one mechanism by which EGCG could ameliorate the effects of SS could be attenuation of TNF-α-cytotoxicity. We examined the effects of EGCG on TNF-α-induced cytotoxicity of the human salivary gland acinar cell line NS-SV-AC using the MTT assay. Results from these experiments are summarized in FIG. 6. EGCG in a dose-dependent manner provided significant protection of NS-SV-AC cells (up to 50%) from TNFα-induced cytotoxicity (two-tailed t-test, p<0.05).

Example 7 p38 MAPK Inhibitor SB203580 and MEK Inhibitor PD98059 Abolished the Protective Effect of EGCG To examine the role of activation of the p38 signaling pathway in reducing TNF-α-induced cytotoxicity, cells were exposed to TNF-[alpha] and EGCG in the presence of either the p38 MAPK inhibitor SB203580 or the MEK inhibitor PD98059. The results of MTT assays indicated that both inhibitors significantly reduced the protective effect of EGCG against TNF-α-induced loss of cell viability (FIG. 7).

Example 8

EGCG Specifically Activates the Phosphorylation of P38 in NS-SV-AC Cells p38 activation is one mechanism by which GTPs attenuates mechanisms of SS pathogenesis. As shown in FIG. 8, EGCG induced a rapid and sustained phosphorylation of p38 in NS-SV-AC cells while, only a slight increase in pERK was detected, and phosphorylation of JNK was not altered. Therefore, of these three signaling pathways, EGCG activates primarily p38 in NS-SV-AC cells.

In the NOD mouse model of SS, oral administration of GTPs lowered the total serum autoantibody level and reduced the magnitude of salivary lymphocyte infiltration. In vitro, EGCC protected acinar-derived cells from TNF-α-induced cytotoxicity. These protective effects of GTPs were associated with the p38 MAPK-signaling pathway.

Example 9

Figure 9:
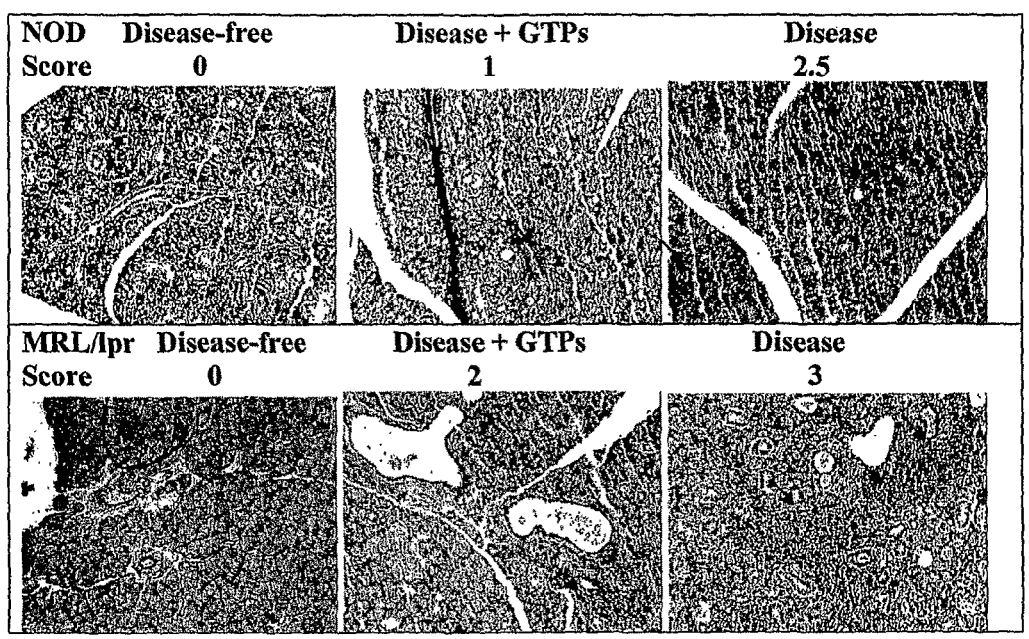
FIG. 9 shows micrographs indicating local lymphocyte infiltration in the submandibular glands of early GTP-treated MRL and NOD mice.

Pathology Scoring of Lymphocyte Infiltration in the Submandibular Glands of Early GTP-treated MRL and NOD Mice FIG. 9 shows representative sections of H&E submandibular glands from each experimental group (disease free, diseased animals treated with GTP, and diseased untreated animals) in both strains, together with the corresponding inflammatory infiltrate score. As shown in FIG. 9, glands from disease-free animals showed cFS of 0; disease plus GTPs a cFS of 1 and 2; and disease a cFS of 2.5 and 3, for NOD and MRL, respectively. These data show a marked in vivo effect of GTPs on the progression and severity of SS-like pathology. Both MRL and NOD mice showed a reduction in focal score, suggesting GTPs effects are not strain specific.

TABLE 1 cDNA microarray determination of autoantigen expression in NHEK treated with 100 μM EGCG for the indicated hours. Numbers represent fold up/down at the time points normalized to time zero levels. Repeats represent different cDNA fragments of one gene. The following autoantigens were not detected: ABCA7, AMPH, ANXA11, ASRGL1, CENPE, CHD3, CHD5, DEAF1, FLJ10613, FLJ12595, GAD1, GAD2, GMEB1, GOLGA6, ICA1, LMOD1, LOC93349, PC, PRTN3, PTPRN, PTPRN2, RCD-8, SC65, SE20-4, SP140, SSA1, STRN, TIGD6, TMPRSS3, and TPX1.

| Autoantigens | 0 | 0.5 h | 2 h | 6 h | 24 h | Descriptions |
|---|---|---|---|---|---|---|
| Inhibited > 2-fold | | | | | | |
| ANAP12 | 1 | 0.505 | 0.991 | 0.4 | 0.198 | *A. kinase* (PRKA) anchor protein (gravin) 12 |
| α-NAC | 1 | 0.632 | 0.521 | 0.0443 | 0.469 | *Homo sapiens* α-NAC gene for nascent polypeptide-associated complex component |
| CENPB | 1 | 0.506 | 0.773 | 0.498 | 0.721 | Centromere protein B |
| CENPC1 | 1 | 1.269 | 0.457 | 0.869 | 0.936 | Centromere protein C 1 |
| FLJ31657 | 1 | 0.833 | 0.608 | 0.435 | 0.959 | Hypothetical protein FLJ31657 |
| FLNB | 1 | 0.72 | 0.92 | 0.875 | 0.243 | Filamin B, γ (actin-binding protein 278) |
| FLNB | 1 | 1.379 | 1.168 | 0.751 | 0.249 | Filamin B, β (actin-binding protein 278) |
| GOLGA1 | 1 | 0.398 | 0.182 | 0.68 | 0.9 | Golgi autoantigen, golgin subfamily a, 1 |
| GOLGA2 | 1 | 0.332 | 0.642 | 0.769 | 0.949 | Golgi autoantigen, golgin subfamily a, 2 |
| GOLGA3 | 1 | 0.533 | 0.58 | 0.547 | 0.419 | Golgi autoantigen, golgin subfamily a, 3 |
| GOLGA4 | 1 | 0.822 | 0.748 | 0.353 | 0.664 | Golgi autoantigen, golgin subfamily a, 4 |
| HSA6591 | 1 | 0.456 | 0.835 | 0.532 | 0.562 | Nucleolar cysteine-rich protein |
| HUMAUANTIG | 1 | 0.948 | 0.779 | 0.444 | 0.517 | Nucleolar GTPase |
| LMO4 | 1 | 0.272 | 0.867 | 0.708 | 1.011 | LIM domain only 4 |
| POLR2A | 1 | 0.13 | 1.29 | 1.80 | 1.02 | Polymerase (RNA) II (DNA-directed) polypeptide A, 220 kDa |
| POLR2A | 1 | 1.03 | 0.45 | 0.44 | 1.17 | Polymerase (RNA) II (DNA-directed) polypeptide A, 220 kDa |
| POLR2D | 1 | 1.14 | 0.95 | 1.04 | 0.29 | Polymerase (RNA) II (DNA-directed) polypeptide D |
| POLR2E | 1 | 0.45 | 0.70 | 0.87 | 0.39 | Polypeptide E, 25 kDa |
| POLR3C | 1 | 0.90 | 0.73 | 0.55 | 0.49 | Polymerase (RNA) III (DNA-directed) (62 kDa) |
| POLR3G | 1 | 1.55 | 1.00 | 1.05 | 0.47 | Polymerase (RNA) III (DNA-directed) (32 kDa) |
| SNRPA | 1 | 1.29 | 0.93 | 1.35 | 0.32 | Small nuclear ribonucleoprotein polypeptide A |
| SP100 | 1 | 1.72 | 1.037 | 0.59 | 0.356 | Nuclear antigen Sp100 |
| SPTAN1 | 1 | 0.41 | 0.75 | 0.56 | 0.42 | Spectrin, α, nonerythrocytic1 (α-fodrin) |
| SPTAN1 | 1 | 0.49 | 0.97 | 0.75 | 0.71 | Spectrin, α, nonerythrocytic1 (α-fodrin) |
| SNRPB | 1 | 0.96 | 0.95 | 0.76 | 0.52 | Small nuclear ribonucleoprotein polypeptides B and B1 |
| SNRPB | 1 | 0.62 | 0.79 | 0.67 | 0.42 | Small nuclear ribonucleoprotein polypeptides B and B1 |
| SNRPB2 | 1 | 0.49 | 0.67 | 0.56 | 0.82 | Small nuclear ribonucleoprotein polypeptide B" |
| SSA2 | 1 | 1.009 | 0.335 | 0.739 | 1.17 | 602540961F1 NIH_MGC_59 *H. sapiens* cDNA clone IMAGE:4671854 5',mRNAsequence |
| SSB | 1 | 0.838 | 0.878 | 0.57 | 0.273 | Sjogren's syndrome antigen B (autoantigen La) |
| SSB | 1 | 0.711 | 0.739 | 0.427 | 0.257 | Sjogren's syndrome antigen B (autoantigen La) |
| STRN3 | 1 | 0.425 | 0.623 | 0.528 | 0.759 | Striatin, calmodulin binding protein 3 |
| TOP1 | 1 | 0.85 | 1.09 | 0.84 | 0.12 | Topoisomerase (DNA) I |
| TOP1 | 1 | 0.62 | 0.62 | 0.33 | 0.43 | Topoisomerase (DNA) I |
| UBTF | 1 | 0.498 | 0.484 | 0.501 | 0.546 | Upstream binding transcription factor, RNA polymerase I |
| Induced then inhibited > 2-fold | | | | | | |
| PMSCL1, 75 kDa | 1 | 3.993 | 1.09 | 0.431 | 0.496 | Polymyositis/scleroderma autoantigen 1 |
| PSME3 | 1 | 2.554 | 1.151 | 1.128 | 0.421 | Proteasome (prosome, macropain) activator subunit 3 (PA28γ; Ki) |

TABLE 1-continued cDNA microarray determination of autoantigen expression in NHEK treated with 100 μM EGCG for the indicated hours. Numbers represent fold up/down at the time points normalized to time zero levels. Repeats represent different cDNA fragments of one gene. The following autoantigens were not detected: ABCA7, AMPH, ANXA11, ASRGL1, CENPE, CHD3, CHD5, DEAF1, FLJ10613, FLJ12595, GAD1, GAD2, GMEB1, GOLGA6, ICA1, LMOD1, LOC93349, PC, PRTN3, PTPRN, PTPRN2, RCD-8, SC65, SE20-4, SP140, SSA1, STRN, TIGD6, TMPRSS3, and TPX1.

| Autoantigens | 0 | 0.5 h | 2 h | 6 h | 24 h | Descriptions |
|---|---|---|---|---|---|---|
| SNRPD1 | 1 | 2.098 | 1.285 | 0.658 | 0.425 | Small nuclear ribonucleoprotein D1 polypeptide, 16 kDa |
| SP100 | 1 | 3.123 | 1.205 | 0.686 | 0.079 | Nuclear antigen Sp100 |
| Induced then declined to control levels | | | | | | |
| ADPRT | 1 | 3.547 | 1.201 | 0.992 | 0.85 | ADP-ribosyltransferase [NAD$^+$; poly(ADP-ribose polymerase] |
| CENPA | 1 | 7.677 | 1.095 | 0.672 | 0.673 | Centromere protein A, 17 kDa |
| MGC5560 | 1 | 4.392 | 1.161 | 1.646 | 0.81 | Hypothetical protein MGC5560 |
| MGC5560 | 1 | 7.07 | 0.932 | 2.605 | 0.552 | Hypothetical protein MGC5560 |
| SP110 | 1 | 5.725 | 1.702 | 1.205 | 0.978 | SP110 nuclear body protein |
| SP110 | 1 | 4.176 | 1.804 | 0.997 | 0.654 | SP110 nuclear body protein |
| SNRP70 | 1 | 3.59 | 1.01 | 2.28 | 0.51 | Small nuclear ribonucleoprotein 70-kDa polypeptide (RNP antigen) |
| XRCC5 | 1 | 2.338 | 1.403 | 0.977 | 0.771 | X-ray repair complementing defective repair in Chinese hamster cells 5 (double-strand break rejoining; Ku autoantigen, 80 kDa) |
| Induced > 2-fold | | | | | | |
| ANXA11 | 1 | 1.043 | 1.26 | 2.141 | 1.946 | Annexin A11 |
| CTDSPL | 1 | 2.83 | 1.12 | 2.42 | 2.10 | Carboxyl-terminal domain, RNA polymerase II, polypeptide A, small phosphatase-like |
| Changed < 2-fold | | | | | | |
| CALR | 1 | 0.71 | 0.943 | 1.482 | 1.528 | Calreticulin |
| CBARA1 | 1 | 0.506 | 0.773 | 0.498 | 0.721 | |
| CHD4 | 1 | 0.766 | 0.811 | 0.916 | 0.84 | Chromodomain helicase DNA-binding protein 4 |
| COL17A1 | 1 | 1.749 | 1.102 | 1.043 | 0.684 | Collagen, type XVII, α 1 |
| CTDSP1 | 1 | 0.71 | 1.00 | 1.25 | 1.39 | Carboxyl-terminal domain, RNA polymerase II, polypeptide A, small phosphatase 1 |
| CTDSP2 | 1 | 1.61 | 1.21 | 0.92 | 1.71 | Carboxyl-terminal domain, RNA polymerase II, polypeptide A, small phosphatase 2 |
| dJ963E22.1 | 1 | 1.842 | 0.864 | 0.723 | 0.88 | Contains the 3' end of a novel gene similar to NY-REN-2 antigen |
| DLAT | 1 | 1.54 | 0.924 | 1.031 | 0.751 | Dihydrolipoamide S-acetyltransferase (E2 component of pyruvate dehydrogenase complex) |
| EPPK1 | 1 | 0.793 | 0.856 | 1.318 | 0.889 | Epiplakin 1 |
| FBL | 1 | 1.64 | 1.12 | 1.09 | 0.69 | Casein kinase II β subunit; complete cds.; fabrillin |
| G22P1 | 1 | 1.15 | 1.185 | 1.127 | 0.792 | Thyroid autoantigen, 70 kDa (Ku antigen) |
| GMEB2 | 1 | 0.584 | 0.739 | 0.626 | 0.745 | Glucocorticoid modulatory element-binding protein 2 |
| GOLGA5 | 1 | 1.566 | 0.928 | 0.731 | 1.494 | Golgi autoantigen, golgin subfamily a, 5 |
| GOLGB1 | 1 | 0.969 | 0.704 | 0.56 | 0.688 | Golgi autoantigen, golgin subfamily b, macrogolgin (with transmembrane signal), 1 |
| HARS | 1 | 1.27 | 1.11 | 0.88 | 0.72 | Histidyl-tRNA synthetase |
| HARSL | 1 | 1.12 | 1.05 | 0.88 | 1.00 | Histidyl-tRNA synthetase-like |
| IMP-2 | 1 | 1.615 | 1.366 | 0.635 | 0.665 | Insulin growth factor-II mRNA-binding protein 2 |
| LAD1 | 1 | 0.799 | 0.681 | 0.954 | 0.553 | Human ladinin (LAD) gene, complete cds. |
| LMO4 | 1 | 0.6 | 1.199 | 1.133 | 0.659 | LIM domain only 4 |
| NS | 1 | 0.634 | 0.95 | 0.519 | 0.814 | Nucleostemin |
| PDHB | 1 | 1.079 | 1.14 | 0.745 | 0.818 | Pyruvate dehydrogenase (lipoamide) β |
| PDX1 | 1 | 1.103 | 0.765 | 0.646 | 0.903 | E3-binding protein |
| PMSCL2 | 1 | 0.959 | 0.938 | 1.058 | 0.717 | Polymyositis/scleroderma autoantigen 2, 100 kDa |
| POLR1B | 1 | 0.67 | 1.03 | 0.98 | 1.04 | Polymerase (RNA) I polypeptide B, 128 kDa |
| POLR1D | 1 | 0.90 | 0.96 | 1.04 | 1.31 | Hypothetical protein MGC9850 |
| POLR2B | 1 | 1.83 | 1.02 | 0.59 | 0.74 | Polymerase (RNA) II (DNA-directed) polypeptide B, 140 kDa |
| POLR2C | 1 | 1.32 | 1.60 | 1.53 | 1.66 | Polymerase (RNA) II (DNA-directed) polypeptide C, 33 kDa |
| POLR2F | 1 | 0.90 | 1.00 | 1.17 | 0.80 | Polymerase (RNA) II (DNA-directed) polypeptide F |
| POLR2G | 1 | 1.09 | 1.02 | 0.74 | 0.89 | Polymerase (RNA) II (DNA-directed) polypeptide G |
| POLR2H | 1 | 0.88 | 0.85 | 1.02 | 1.15 | Polymerase (RNA) II (DNA-directed) polypeptide H |
| RALY | 1 | 1.556 | 0.752 | 1.496 | 0.612 | RNA-binding protein (autoantigenic, human RNP-associated with lethal yellow) |
| SART1 | 1 | 1.982 | 1.188 | 1.462 | 0.98 | Squamous cell carcinoma antigen recognized by T cells |
| SLC25A16 | 1 | 1.022 | 0.886 | 1.099 | 1.144 | H. sapiens, similar to cytochromec-like antigen, clone MGC:2960 IMAGE:3139311, mRNA, complete cds. |
| SNRPD1 | 1 | 0.755 | 0.676 | 0.612 | 0.517 | Small nuclear ribonucleoprotein D1 polypeptide, 16 kDa |
| SNRPC | 1 | 1.28 | 1.08 | 1.28 | 1.12 | Small nuclear ribonucleoptorein polypeptide C |
| SOX13 | 1 | 1.304 | 0.771 | 1.24 | 1.582 | SRY-box 13 |
| SP110 | 1 | 1.149 | 1.026 | 0.7 | 0.621 | SP110 nuclear body protein |
| SPTBN | 1 | 0.91 | 0.92 | 0.95 | 0.72 | Spectrin, β nonerythrocytic 1 |
| SSA2 | 1 | 0.709 | 0.919 | 0.687 | 0.88 | autoantigen SS-A/Ro) |
| SSA2 | 1 | 0.505 | 0.957 | 0.571 | 1.556 | H. sapiens cDNA FLJ13982 fis, clone Y79AA1001711, highly similar to human 60-kDa ribonucleoprotein (Ro) mRNA |

TABLE 1-continued cDNA microarray determination of autoantigen expression in NHEK treated with 100 μM EGCG for the indicated hours. Numbers represent fold up/down at the time points normalized to time zero levels. Repeats represent different cDNA fragments of one gene. The following autoantigens were not detected: ABCA7, AMPH, ANXA11, ASRGL1, CENPE, CHD3, CHD5, DEAF1, FLJ10613, FLJ12595, GAD1, GAD2, GMEB1, GOLGA6, ICA1, LMOD1, LOC93349, PC, PRTN3, PTPRN, PTPRN2, RCD-8, SC65, SE20-4, SP140, SSA1, STRN, TIGD6, TMPRSS3, and TPX1.

| Autoantigens | 0 | 0.5 h | 2 h | 6 h | 24 h | Descriptions |
| --- | --- | --- | --- | --- | --- | --- |
| SSA2 | 1 | 0.596 | 0.98 | 0.85 | 0.94 | *H. sapiens* cDNA FLJ13982 fis, clone Y79AA1001711, highly similar to human 60-kDa ribonucleoprotein (Ro) mRNA |
| SSNA1 | 1 | 1.354 | 1.17 | 1.608 | 0.943 | Sjogren's syndrome nuclear autoantigen 1 |
| SSSCA1 | 1 | 1.267 | 1.694 | 1.005 | 1.228 | Sjogren's syndrome/scleroderma autoantigen 1 |
| XRCC5 | 1 | 1.87 | 1.141 | 0.958 | 0.725 | X-ray repair complementing defective repair in Chinese hamster cells 5 (double-strand break rejoining; Ku autoantigen, 80 kDa) |

What is claimed is:

1. A method for treating one or more symptoms of Sjögren's syndrome in a human subject comprising
administering to a subject in need thereof one or more green tea polyphenols in an amount effective to decrease expression of one or more autoantigens in one or more salivary gland cells of the subject, wherein the one or more symptoms of Sjögren's syndrome are selected from the group consisting of xerostomia and xerophthalmia.

2. The method of claim 1, wherein the one or more green tea polyphenols comprise (−)-epigallocatechin-3-gallate or a pharmaceutically acceptable salt thereof.

3. The method of claim 1, wherein the autoantigen is selected from the group consisting of SS-A, SS-B, fodrin, centromere protein, golgin-67, coilin, and Poly (ADP-ribose) polymerase (PARP).

4. The method of claim 1, wherein the one or more green tea polyphenols comprise (−)-epicatechin, (−)-epigallocatechin, (−)-epicatechin-3-gallate, proanthocyanidins combinations thereof.

5. The method of claim 1, wherein expression of at least two autoantigens is decreased relative to a control.

* * * * *